US012788762B2

(12) United States Patent
Nagy et al.

(10) Patent No.: US 12,788,762 B2
(45) **Date of Patent: *Nov. 10, 2026**

(54) AZELASTINE AS ANTIVIRAL TREATMENT

(71) Applicant: CEBINA GmbH, Vienna (AT)

(72) Inventors: Eszter Nagy, Vienna (AT); Gábor Nagy, Sopron (HU); Valeria Szijarto, Vienna (AT); Robert Konrat, Vienna (AT)

(73) Assignee: CEBINA GMBH, Vienna (AT)

( * ) Notice: Subject to any disclaimer, the term of this patent is extended or adjusted under 35 U.S.C. 154(b) by 685 days.

This patent is subject to a terminal disclaimer.

(21) Appl. No.: 17/928,422

(22) PCT Filed: May 28, 2021

(86) PCT No.: PCT/EP2021/064338

§ 371 (c)(1),
(2) Date: Nov. 29, 2022

(87) PCT Pub. No.: WO2021/239943

PCT Pub. Date: Dec. 2, 2021

(65) Prior Publication Data

US 2023/0201216 A1 Jun. 29, 2023

(30) Foreign Application Priority Data

May 29, 2020 (EP) .................................... 20177451
Jul. 8, 2020 (EP) .................................... 20184767
Sep. 11, 2020 (EP) .................................... 20195740
Apr. 29, 2021 (EP) .................................... 21171333

(51) Int. Cl.
*A61K 31/55* (2006.01)
*A61K 9/00* (2006.01)
*A61K 45/06* (2006.01)
*A61P 31/14* (2006.01)

(52) U.S. Cl.
CPC ............ *A61K 31/55* (2013.01); *A61K 9/0043* (2013.01); *A61K 9/0073* (2013.01); *A61K 45/06* (2013.01); *A61P 31/14* (2018.01)

(58) Field of Classification Search
CPC ...................................................... A61K 31/55
USPC .......................................................... 514/215
See application file for complete search history.

(56) References Cited

U.S. PATENT DOCUMENTS 5,164,194 A * 11/1992 Hettche .................. A61P 27/14
514/217.05
8,003,127 B2 8/2011 Liversidge et al.
8,642,069 B2 * 2/2014 Goldin .................. A61K 45/06
424/45
11,433,080 B2 * 9/2022 Nagy .................. A61K 9/0043
2010/0152147 A1 6/2010 Fuge et al.
2010/0311656 A1 12/2010 Rudolph et al.

FOREIGN PATENT DOCUMENTS

CN 101591228 B 9/2013
CN 113521289 A 10/2021
DE 3836579 A1 * 5/1989 ............ A61K 31/55
JP 2008285474 A 11/2008
WO 2010/025236 A1 3/2010
WO 2010/1010649 A2 9/2010

OTHER PUBLICATIONS

Astelin: Package Insert/Prescribing Info, Drugs.com, U.S. Approved 1996, accessed Aug. 11, 2025 (Year: 1996).*
Gordon et al., A SARS-CoV-2 protein interaction map reveals targets for drug repurposing, Nature, Apr. 30, 2020, vol. 583, pp. 459-467 (Year: 2020).*
Luers et al., Olfactory and Gustatory Dysfunction in Coronavirus Disease 2019 (COVID-19), Clinical Infectious Diseases, May 1, 2020, vol. 71, pp. 2262-2264 (Year: 2020).*
Astelin, Astelin: Package Insert/Prescribing Info, Drugs.com, U.S. Approved 1996, accessed Aug. 11, 2025 (Year: 1996).*
Examination Report for corresponding European Patent Application No. 22206040.2 (May 20, 2025).
Extended Search Report for related European Patent Application No. 20184767.0 (Dec. 10, 2020).
Extended Search Report for corresponding European Patent Application No. 22206040.2 (Apr. 27, 2023).
Examination Report for related European Patent Application No. 2206040.2 (May 20, 2025).
Examination Report for related European Patent Application No. 217271865 (Feb. 7, 2022).
Office Action for related U.S. Appl. No. 17/333,857 (Sep. 10, 2021).
Adedeji et al., "Novel Inhibitors of Severe Acute Respiratory Syndrome CoronavirusEntry That Act by Three Distinct Mechanisms," J. Virology, vol. 87(14):8017-8028 (2013).
Fu et al., "In silico analysis and experimental validation of azelastine hydrochloride (N4)targeting sodium taurocholate co-transporting polypeptide (NTCP) in HBVtherapy," Cell Prolif., 47:326-335 (2014).
Gregori-Pulgjané, "SHED: Shannon Entropy Descriptors from To.pological Feature Distributions." J. Chem Inf. Model, 46:1615-1622 (2006).
Guruprasad, "Human SARS CoV-2 spike protein mutations," Proteins, 2021, DOI: 10.1002/prot.26042, pp. 1-8.
Gysi, et al., "Network medicine framework for identifying drug repurposing opportunities for COVID-19," PNAS, 118 (19):e2025581118 (2021).
Gysi, et al., "Network medicine framework for identifying drug repurposing opportunities for COVID-19," arXiv:2004.07229v1 [q-bio.MN], Apr. 15, 2020.

(Continued)

*Primary Examiner* — Jeffrey H Murray
*Assistant Examiner* — Rilla Marie Samsell
(74) *Attorney, Agent, or Firm* — Michael Fedrick; LOZA & LOZA, LLP

(57) ABSTRACT

An Azelastine compound in an antiviral effective amount for use as an antiviral substance in a pharmaceutical preparation for use in prophylactic or therapeutic treatment of a subject in need of antiviral treatment.

25 Claims, 13 Drawing Sheets

Figure 1A:
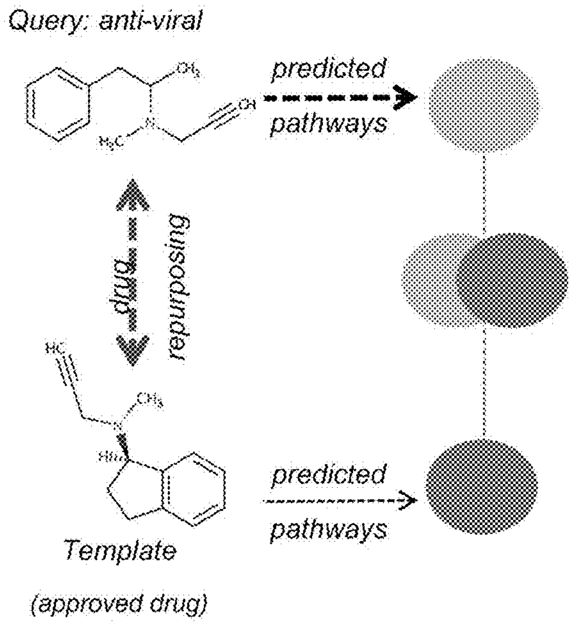

Specification includes a Sequence Listing.

(56) References Cited

OTHER PUBLICATIONS

He et al., "Identification of diverse alphacoronaviruses and genomic characterization of a novel severe acute respiratory syndrome-like coronavirus from bats in China," J. Virology, vol. 88(12):7070-7082 (2014).

Konrat et al., "The Anti-histamine Azelastine, Identified by Computational Drug Repurposing, Inhibits SARS-CoV-2 Infection in Reconstituted Human Nasal Tissue In Vitro," bioRxiv, doi: https://doi.org/10.1101/2020.09.15.296228 (Sep. 15, 2020).

Odhar et al., "Molecular docking and dynamics simulation of FDAapproved drugs with the main protease from 2019 novel coronavirus," Bioinformation, 16(3):236-244 (2020).

Raghav et al., "Analysis of Indian SARS-CoV-2 genomes reveals prevalence of of D614G Mutation in Spike Protein Predicting an Increase in Interaction With TMPRSS2 and Virus Infectivity," Front. Microbiol. Sec. Virology, vol. 11, Article 594928 (Nov. 22, 2020).

Riepler et al., "Comparison of Four SARS-CoV-2 Neutralization Assays." Vaccines 9, 13, https://dx.doi.org/10.3390/vaccines9010013 (2021).

Simon, "Efficacy of Azelastine in the Treatment of Allergic and Infectious Inflammatory Rhinitis in Childhood," Pediatric Asthma, Allergy & Immunology, 12(3):199-206 (1998).

Simon, "Efficacy of Azelastine in the Prophylaxis of Acute Upper Respiratory Tract Infections," Pediatric Asthma, Allergy & Immunology, 16(4):275-282 (2003).

Office Action in corresponding Russian Patent Application No. 2022133013/04 (071853), dated Oct. 9, 2024, 24 pages.

Azelastine, "FDA Prescribing Information, Side Effects and Uses", drugs.com, 2016, pp. 1-17 https://web. archive.org/web/20160820225031/https://www.drugs.com/pro/azelastine.html.

International Search Report for International Patent Application No. PCT/EP2021/064338, dated Sep. 22, 2021.

International Written Opinion for International Patent Application No. PCT/EP2021/064338, dated Sep. 22, 2021.

International Preliminary Report on Patentability for International Patent Application No. PCT/EP2021/064338, dated Apr. 28, 2022.

Saudi Arabia Office Action, SA Patent Application No. 522441507, May 31, 2025, 6 pgs.

Office Action, Australian Patent Application No. 2021279280, Apr. 1, 2026.

Office Action issued in corresponding Indian Patent Application No. 121113245365 (Jul. 15, 2026).

Horbal, et al. "Azelastine Hci: A Review of the Old and New Formulations." Clinical Medicine Insights: Therapeutics, 2010, vol. 2, pp. 432-438.

McNeely, et al. "Intranasal Azelastine A Review of its Efficacy in the Management of Allergic Rhinitis." Drugs, 1998, 56 (1): 91-114.

* cited by examiner

A: uninfected (negative) control
B: virus infected (positive) control
C: virus + 3.125 μM Azelastine-HCl
D: virus + 6.25 μM Azelastine-HCl
E: virus + 12.5 μM Azelastine-HCl
F: virus + 25 μM Azelastine-HCl

FIG. 5

SEQ ID NO:4: SARS-CoV-2, S-protein

NCBI accession number QII57161.1 (human SARS-CoV-2, S-protein)
MFVFLVLLPLVSSQCVNLTTRTQLPPAYTNSFTRGVYYPDKVFRSSVLHSTQDLFLPFFSNVTWFHAIHV
SGTNGTKRFDNPVLPFNDGVYFASTEKSNIIRGWIFGTTLDSKTQSLLIVNNATNVVIKVCEFQFCNDPF
LGVYYHKNNKSWMESEFRVYSSANNCTFEYVSQPFLMDLEGKQGNFKNLREFVFKNIDGYFKIYSKHTPI
NLVRDLPQGFSALEPLVDLPIGINITRFQTLLALHRSYLTPGDSSSGWTAGAAAYYVGYLQPRTFLLKYN
ENGTITDAVDCALDPLSETKCTLKSFTVEKGIYQTSNFRVQPTESIVRFPNITNLCPFGEVFNATRFASV
YAWNRKRISNCVADYSVLYNSASFSTFKCYGVSPTKLNDLCFTNVYADSFVIRGDEVRQIAPGQTGKIAD
YNYKLPDDFTGCVIAWNSNNLDSKVGGNYNYLYRLFRKSNLKPFERDISTEIYQAGSTPCNGVEGFNCYF
PLQSYGFQPTNGVGYQPYRVVVLSFELLHAPATVCGPKKSTNLVKNKCVNFNFNGLTGTGVLTESNKKFL
PFQQFGRDIADTTDAVRDPQTLEILDITPCSFGGVSVITPGTNTSNQVAVLYQDVNCTEVPVAIHADQLT
PTWRVYSTGSNVFQTRAGCLIGAEHVNNSYECDIPIGAGICASYQTQTNSPRRARSVASQSIIAYTMSLG
AENSVAYSNNSIAIPTNFTISVTTEILPVSMTKTSVDCTMYICGDSTECSNLLLQYGSFCTQLNRALTGI
AVEQDKNTQEVFAQVKQIYKTPPIKDFGGFNFSQILPDPSKPSKRSFIEDLLFNKVTLADAGFIKQYGDC
LGDIAARDLICAQKFNGLTVLPPLLTDEMIAQYTSALLAGTITSGWTFGAGAALQIPFAMQMAYRFNGIG
VTQNVLYENQKLIANQFNSAIGKIQDSLSSTASALGKLQDVVNQNAQALNTLVKQLSSNFGAISSVLNDI
LSRLDKVEAEVQIDRLITGRLQSLQTYVTQQLIRAAEIRASANLAATKMSECVLGQSKRVDFCGKGYHLM
SFPQSAPHGVVFLHVTYVPAQEKNFTTAPAICHDGKAHFPREGVFVSNGTHWFVTQRNFYEPQIITTDNT
FVSGNCDVVIGIVNNTVYDPLQPELDSFKEELDKYFKNHTSPDVLGDISGINASVVNIQKEIDRLNEVA
KNLNESLIDLQELGKYEQYIKWPWYIWLGFIAGLIAIVMVTIMLCCMTSCCSCLKGCCSCGSCCKFDEDD
SEPVLKGVKLHYT

SEQUENCE LISTING

```
<160> NUMBER OF SEQ ID NOS: 19

<210> SEQ ID NO 1
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: R
<222> LOCATION: (3)..(3)
<223> OTHER INFORMATION: is G/A
<220> FEATURE:
<221> NAME/KEY: S
<222> LOCATION: (12)..(12)
<223> OTHER INFORMATION: is G/C

<400> SEQUENCE: 1

caratgttaa asacactatt agcata                                          26


<210> SEQ ID NO 2
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: R
<222> LOCATION: (5)..(5)
<223> OTHER INFORMATION: is G/A

<400> SEQUENCE: 2

gtgaratggt catgtgtggc gg                                              22


<210> SEQ ID NO 3
```

-continued

<211> LENGTH: 25
<212> TYPE: DNA
<213> ORGANISM: Artificial Sequence
<220> FEATURE:
<223> OTHER INFORMATION: Probe

<400> SEQUENCE: 3
caggtggaac ctcatcagga gatgc 25

<210> SEQ ID NO 4
<211> LENGTH: 1273
<212> TYPE: PRT
<213> ORGANISM: SARS-CoV-2

<400> SEQUENCE: 4

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala
275 280 285

Val Asp Cys Ala Leu Asp Pro Leu Ser Glu Thr Lys Cys Thr Leu Lys
290 295 300

Ser Phe Thr Val Glu Lys Gly Ile Tyr Gln Thr Ser Asn Phe Arg Val
305 310 315 320

Gln Pro Thr Glu Ser Ile Val Arg Phe Pro Asn Ile Thr Asn Leu Cys

-continued

```
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750
```

```
Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155
```

-continued

```
His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270


<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5

acaggtacgt taatagttaa tagcgt                                          26


<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6

atattgcagc agtacgcaca c                                               21


<210> SEQ ID NO 7
<211> LENGTH: 26
<212> TYPE: DNA
<213> ORGANISM: Artificial Sequence
<220> FEATURE:
<223> OTHER INFORMATION: Probe

<400> SEQUENCE: 7

acactagcca tccttactgc gcttcg                                          26


<210> SEQ ID NO 8
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: R
<222> LOCATION: (5)..(5)
<223> OTHER INFORMATION: is G/A

<400> SEQUENCE: 8

gtgaratggt catgtgtggc gg                                              22


<210> SEQ ID NO 9
<211> LENGTH: 25
```

<212> TYPE: DNA
<213> ORGANISM: Artificial Sequence
<220> FEATURE:
<223> OTHER INFORMATION: Probe

<400> SEQUENCE: 9
caggtggaac ctcatcagga gatgc 25

<210> SEQ ID NO 10
<211> LENGTH: 26
<212> TYPE: DNA
<213> ORGANISM: Artificial Sequence
<220> FEATURE:
<223> OTHER INFORMATION: Probe
<220> FEATURE:
<221> NAME/KEY: W
<222> LOCATION: (9)..(9)
<223> OTHER INFORMATION: is A/T
<220> FEATURE:
<221> NAME/KEY: M
<222> LOCATION: (18)..(18)
<223> OTHER INFORMATION: is A/C

<400> SEQUENCE: 10
ccaggtggwa crtcatcmgg tgatgc 26

<210> SEQ ID NO 11
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: R
<222> LOCATION: (3)..(3)
<223> OTHER INFORMATION: is G/A
<220> FEATURE:
<221> NAME/KEY: S
<222> LOCATION: (12)..(12)
<223> OTHER INFORMATION: is G/C

<400> SEQUENCE: 11
caratgttaa asacactatt agcata 26

<210> SEQ ID NO 12
<211> LENGTH: 26
<212> TYPE: DNA
<213> ORGANISM: Artificial Sequence
<220> FEATURE:
<223> OTHER INFORMATION: Primer

<400> SEQUENCE: 12
acaggtacgt taatagttaa tagcgt 26

<210> SEQ ID NO 13
<211> LENGTH: 26
<212> TYPE: DNA
<213> ORGANISM: Artificial Sequence
<220> FEATURE:
<223> OTHER INFORMATION: Probe

<400> SEQUENCE: 13
acactagcca tccttactgc gcttcg 26

<210> SEQ ID NO 14
<211> LENGTH: 22
<212> TYPE: DNA
<213> ORGANISM: Artificial Sequence
<220> FEATURE:

-continued

```
<223> OTHER INFORMATION: Primer

<400> SEQUENCE: 14

atattgcagc agtacgcaca ca                                    22


<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15

cacattggca cccgcaatc                                        19


<210> SEQ ID NO 16
<211> LENGTH: 25
<212> TYPE: DNA
<213> ORGANISM: Artificial Sequence
<220> FEATURE:
<223> OTHER INFORMATION: Probe

<400> SEQUENCE: 16

acttcctcaa ggaacaacat tgcca                                 25


<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17

gaggaacgag aagaggcttg                                       20


<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18

agatcaactt ctgtcatcca gcaa                                  24


<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19

gcacatcata attaggagta tcaat                                 25
```

AZELASTINE AS ANTIVIRAL TREATMENT

CROSS-REFERENCE TO RELATED APPLICATIONS

This application is the U.S. national stage of International Patent Application No. PCT/EP2021/064338, filed on May 28, 2021 and entitled AZELASTINE AS ANTIVIRAL TREATMENT, which claims the benefit of priority under 35 U.S.C. § 119 from the following European patent applications: European Patent Application No. 20177451.0, filed on May 29, 2020; European Patent Application No. 20184767.0, filed on Jul. 8, 2020; European Patent Application No. 20195740.4, filed on Sep. 11, 2020; and European Patent Application No. 21171333.4, filed on Apr. 29, 2021. The disclosures of the foregoing applications are incorporated herein by reference in their entirety.

SEQUENCE LISTING

The entire content of a Sequence Listing titled "Sequence_Listing.txt," created on Nov. 28, 2022 and having a size of 15 kilobytes, which has been submitted in electronic form in connection with the present application, is hereby incorporated by reference herein in its entirety.

FIELD OF THE INVENTION

The present invention relates to novel uses of an antihistamine drug compound for treating viral infections, particularly methods and compounds for treating Coronaviridae infections (e.g., SARS virus or MERS virus), adenovirus infections, human Respiratory Syncytial Viral infections and influenza infections.

BACKGROUND OF THE INVENTION

Coronaviruses are single-stranded RNA viruses, about 120 nanometers in diameter. They are prone to mutation and recombination and are therefore highly diverse. There are about 40 different varieties and they mainly infect human and non-human mammals and birds. They reside in bats and wild birds, and can spread to other animals and hence to humans.

There are four main genera (alpha, beta, gamma, and delta-coronavirus) based on their genomic structure. Alpha- and beta-coronaviruses infect only mammals, usually causing respiratory symptoms in humans and gastroenteritis in other animals. Until December of 2019, only six different coronaviruses were known to infect humans. Four of these (HCoV-NL63, HCoV-229E, HCoV-OC43 and HKU1) usually caused mild common cold-type symptoms in immunocompetent people and the other two have caused pandemics in the past two decades. In 2002-2003, the severe acute respiratory syndrome coronavirus (SARS-CoV) caused a SARS epidemic that resulted in a 10% mortality. Similarly, the Middle East respiratory syndrome coronavirus (MERS-CoV) caused a pandemic in 2012 with a 37% mortality rate.

In late 2019 and early 2020, a novel coronavirus, SARS-coronavirus 2 (SARS-CoV-2), which is closely related to SARS-CoV, was discovered to be the cause of a large and rapidly spreading outbreak of respiratory disease, including pneumonia. Since the novel coronavirus was recognized, the disease it caused was termed coronavirus disease 2019 (CoVID-19).

The SARS-related coronaviruses are covered by spike proteins that contain a variable receptor-binding domain (RBD). This RBD binds to angiotensin-converting enzyme-2 (ACE-2) receptor found in the heart, lungs, kidneys, and gastrointestinal tract, thus facilitating viral entry into target cells.

The original virus strain spread from Wuhan is considered as the "wild-type" virus, which soon gave rise to variants, i.e. mutants that evolved through natural selection based on higher infectivity. In early March 2020, a variant with D614G mutation in the spike protein (B.1 variant) were identified in Europe, which soon replaced the original Wuhan strain globally. Subsequently, SARS-CoV-2 variants B.1.1.7 (also known as 20I/501Y.V1, VOC 202012/01) and B.1.351 (also known as 20H/501Y.V2) were identified in the United Kingdom and South Africa, respectively, and have since spread to many countries. These variants harbor diverse mutations in the gene encoding the spike protein. One of these is in the receptor binding domain (RBD which binds human ACE2) at position 501, where the amino acid asparagine (N) has been replaced with tyrosine (Y) (mutation N501Y). The B.1.1.7 variant also has several other mutations, including: 69/70 deletion and likely leads to a conformational change in the spike protein, and P681H, near the S1/S2 furin cleavage site. The combination of these mutations leads to higher receptor binding, more efficient spread and higher disease-causing potential compared to the original version that emerged in Wuhan in China in 2019. The B.1.351 variant has in addition to the N501Y, also the E484K and K417N mutations, but not the 69/70 deletion. Several lines of evidence suggest that this variant emerged due to immune pressure i.e. as an escape from the human immune response resulting from natural infection, or passive immune therapy or active immunization with different vaccines. The E484K mutation seems to be responsible for reduced vaccine effectiveness. This mutation (along with 16 other mutations N501Y and K417T) was also detected in the Brazilian variant, designated as P.1. Variant P.1. caused widespread infection in Brazil and was later detected globally. This mutant is suspected to cause more severe disease in younger people, lead to higher mortality and evade immune response induced by the previous variant and some of the vaccines.

The mutant B.1.617 was first detected and spread in India. It has 13 mutations from those 3 are of concern regarding immune evasion: E484Q, L452R and P681R. The lineage B.1.618 became one of the dominant mutants in West Bengal, it carries the deletion of two amino acids (H146del and Y145del), as well as the E484K and D614G mutations in the spike protein. It is speculated to possess higher infectivity and pose a threat for evading natural or vaccine induced immunity.

It is highly likely that wide-spread vaccination will induce the emergence of further variants with different combination of the currently known and new mutations.

The accelerated global vaccination together with the simultaneous intense spread of the virus poses a huge evolutionary pressure for the emergence of escape mutants. All vaccines, almost exclusively, rely on triggering an immune response against the spike protein. Furthermore, according to the current view, a neutralizing immune response against the receptor binding domain of the spike protein is considered to be the major contributor to protection. Based on these two facts, among the naturally emerging virus variants those will be selected that express mutated spike proteins affording a selective advantage (higher binding to the receptor and/or evasion of the neutralizing immune response). Subsequent variants may accumulate several successive mutations, with higher overall virulence/ transmissibility and/or with a higher likelihood of immune evasion. It is envisioned that besides those mentioned above additional new virus variants will emerge with the potential need of second-generation vaccines for optimal protection against them.

Therefore, antiviral compounds active against the, by now dominant UK (B1.1.7) variant and the SA (B.1.351) variant as well as against other emerging variants that are associated with greatly reduced vaccine-induced protection, are highly relevant, both for prevention and treatment.

Adenoviruses are large non-enveloped viruses with a double-stranded DNA genome. The family Adenoviridae contains six genera with broad host specificity of viruses. All seven human adenovirus families (A to G) belong to the Mastadenovirus genus. Currently, the human viruses are classified into 88 different (sero)types, which are responsible to cause various mucosal infections. Types within families B (HAdV-B) and C (HAdV-C) are responsible for upper respiratory tract infections, HAdV-F (mainly types 40 and 41) and HAdV-G (mainly type 52) types cause gastroenteritis. Conjunctivitis is associated with HAdV-B and HAdV-D. These mucosal infections are usually self-limiting but can be more severe in an immunocompromised host. Adenovirus serotype 14 is an emerging pathogen that cause outbreaks of severe respiratory infections that could be lethal even in immunocompetent hosts.

Adenoviruses exhibit a classical icosahedral capsid made of 240 hexon and 12 penton proteins. The penton bases are associated with protruding fibers that bind to the host cell receptors: CD46 (family B) and coxsackie/adenovirus receptor (CAR, for all other families). This initial binding is followed by the interaction of the penton base viral structures with αV integrins, which stimulates endocytosis of the virus particles. Intracellularly, the capsid is destabilized, the endosome is degraded, and the viral DNA enters the nucleus through the nuclear pore. After associating with histone proteins the host transcription machinery is used for viral gene expression without the integration of the viral genome into the host genome. Viral proteins are expressed in an early (mainly regulatory proteins) and late (structural proteins) separated by the genome replication. Finally, the viral genomes are packaged into the protein shell and released from the host cell upon a virus induced lysis procedure.

Adenoviruses are relatively resistant to disinfectants and detergents (non-encapsulated), and survive long on surfaces and in water. There are no proven antiviral drugs to treat adenoviral infections, so treatment is largely directed at the symptoms. Currently, there is no adenovirus vaccine available to the general public, but a vaccine was used by the US military for types 4 and 7. Recently, engineered adenoviruses were successfully used in gene therapy and as viral vectors for heterologous vaccine antigen delivery (Ebola and Covid).

Human Respiratory Syncytial Virus (hRSV) is an enveloped virus with a negative-sense, single-stranded RNA genome. The genome is linear and has 10 genes encoding for 11 proteins. RSV is divided into two antigenic subtypes, A and B, with 16 and 22 clades (or strains), respectively.

RSV is highly contagious and can cause outbreaks from both community and hospital transmission. Each year, approximately 30 million acute respiratory illnesses and over 60,000 childhood deaths are caused RSV worldwide. Transmission occurs through contaminated aerosol droplets encountering mucosal surfaces of the nose, mouth, or eyes. Infection of the ciliated cells of the upper airways is followed by spread to the lower airways. It is among the most common childhood infections of various severity ranging from mild upper respiratory tract infection through bronchiolitis to viral pneumonia, which in the most severe cases may require mechanical ventilation. Immunocompromised individuals (including pre-term infants) have a higher risk for more severe diseases outcome. Therapeutic options are usually limited to supportive care, although ribavirin has been licensed for RSV infections in children. Vaccines are not available (despite significant development efforts), however, passive immunization with monoclonal antibodies (palivizumab) has become available as a choice for prophylaxis.

Influenza, commonly called "the flu", is an infectious disease caused by influenza viruses. In each season (winter months in the Northern hemisphere) 5-15% of the population contracts influenza, with approx. 3-5 million severe cases. Over half a million deaths occur annually among high-risk groups, including young children, the elderly, and people with chronic health conditions. Following a 1-4 days incubation period, the onset of symptoms is sudden including fever, chills, headaches, muscle pain or aching, loss of appetite, fatigue, and confusion. Pneumonia may be caused by the primary viral infection or by a secondary bacterial infection, such as by the pneumococcus or *S. aureus*. Transmission of influenza is mediated by aerosol droplets. The primary infection site is the upper airways followed by progression to the lower airways and invasive infection.

There are four types (species) of influenza viruses: A, B, C and D. Seasonal epidemics (i.e. flu season) is caused by human influenza A (IAV) and B (IBV) viruses, while C and D are rarely associated with symptomatic infections in humans. Influenza A viruses are divided into subtypes based on two proteins on the surface of the virus: hemagglutinin (H) and neuraminidase (N). Although there are potentially 198 different influenza A subtype combinations, currently H1N1 and H3N2 types circulate worldwide. Influenza B viruses are not divided into subtypes, but instead are further classified into two lineages: B/Yamagata and B/Victoria. Based on these, seasonal flu vaccines usually contain two A (an H1N1 and an H3N2) and one or two B strains in combination. Influenza viruses have a negative-sense, single-stranded RNA genome that is segmented. Both IAV and IBV contain 8 segments, that could combine with the genome of other influenza viruses upon co-infection of the same cell. This process (called reassortment) give rise to progeny with significantly altered viral antigen composition. Such reassortant virus variants are novel to the human population and may give rise to pandemics (e.g., the Spanish flu in 1918, H1N1). Reassortment may also occur between viruses specific to different hosts. For instance, the "swine flu" pandemic in 2009 was caused by a triple reassortant virus carrying a combination of swine-, avian- and human-specific virus sequences (H1N1. Similarly, avian influenza strains, which are common in wild-water birds occasionally infect humans ("avian or bird flu", H5N1). Upon reassortment of such avian viruses with human influenza viruses may give rise to variants enabling human-to-human spread, and therefore, have the potential to cause global pandemics.

Therapy of individuals of lower risk groups mainly focuses on symptomatic treatment (fever) and isolation. Patients suffering in severe or progressive clinical illness associated with suspected or confirmed influenza virus infection are treated with antiviral drugs (e.g., oseltamivir or other neuraminidase inhibitors) and supportive therapy (e.g. anti-inflammatory drugs). High risk groups (elderly, pregnant women, immunocompromised, associated chronic diseases) should receive annual seasonal flu vaccines as prophylaxis.

Azelastine, a phthalazine derivative, is an antihistamine available as an intranasal spray for the treatment of allergic and vasomotor rhinitis and as an ophthalmic solution for the treatment of allergic conjunctivitis. It is a racemic mixture, though there is no noted difference in pharmacologic activity between enantiomers, and was first granted FDA approval in 1996.

Gysi et al. ("Network Medicine Framework for Identifying Drug Repurposing Opportunities for COVID-19", arXiv:2004.07229 [q-bio.MN] dated 15 Apr. 2020) discloses a network-based toolset to COVID-19 to arrive at certain drug candidates based on their likely efficacy for COVID-19 patients, among them Azelastine, yet without any indication whether the antihistamine would have a direct impact on the virus underlying the disease.

Hasanain Abdulhameed Odhar et al. (Bioinformation 2020, 16(3):236-244) describe molecular docking and dynamics simulation of FDA approved drugs with the main protease from 2019 novel coronavirus. Drugs were ranked according to their minimum binding activity to main protease crystal of 2019-nCoV, with Azelastine being ranked less preferred than Conivaptan.

Xia Xiao et al. (bioRxiv Jul. 6, 2020, DOI:10.1101/2020.07.06.188953) describe antiviral activity of a series of compounds against OC43, among them Azelastine as an anti-histamine.

Fu et al. (Cell Prolif. 2014, 47:326-335) disclose azelastine hydrochloride targeting sodium taurocholate co-transporting polypeptide (NTCP) in hepatitis B virus (HBV) therapy. NTCP is a transmembrane protein highly expressed in human hepatocytes that mediates the transport of bile acids, which plays a key role in HBV entry into hepatocytes.

M. W. Simon (Pediatric Asthma, Allergy & Immunology, 2003, Vol. 16:275-282) describes azelastine as a potent and selective second-generation histamine $H_1$ receptor antagonist that downregulates expression of the intracellular adhesion molecule-1 (ICAM-1) receptor, which plays an important role in human rhinovirus, Coxsackie type A viruses, adenovirus type 5, human parainfluenza virus type 2 and 3, and respiratory syncytial virus mucosal attachment as well as mobilization of immune effector cells.

SUMMARY OF THE INVENTION

It is the objective of the present invention to provide new antiviral treatments, medicinal and pharmaceutical products which can be used to prevent from virus infection and/or virus spread, in particular in subjects that have been exposed to or infected with a virus, or who are at risk of being infected. The objective is solved by the subject of the present claims and as further described herein.

The invention provides for an Azelastine compound in an antiviral effective amount for use as an antiviral substance in a pharmaceutical preparation for use in prophylactic or therapeutic treatment of a subject in need of antiviral treatment.

Specifically, the Azelastine compound is Azelastine, or a pharmaceutically acceptable salt thereof, such as Azelastine hydrochloride.

According to a specific aspect, the pharmaceutical preparation is a medicinal product or a drug product. Specifically, the pharmaceutical preparation comprises the Azelastine compound and a pharmaceutically acceptable carrier.

Specifically, the subject is need of antiviral treatment targeting a respiratory virus, such as influenza virus, respiratory syncytial virus, adenovirus, coronavirus, or upper respiratory tract virus, such as rhinovirus.

A respiratory virus is herein specifically understood to be a virus causing respiratory disease. Though some of the target viruses further described herein may not only cause a respiratory disease, but also affect other body parts, such viruses are herein still understood to be a "respiratory virus". Specifically, the antiviral treatment is targeting one or more human viruses, in particular a human respiratory virus, such as selected from the virus families Coronaviridae, Adenoviridae, Paramyxoviridae or Orthomyxoviridae.

Specifically, a disease condition is treated which is caused by or associated with an infection by one or more of:

a) Coronaviridae viruses, preferably selected from the group consisting of a β-coronavirus, such as SARS-CoV-2, MERS-CoV, SARS-CoV-1, HCoV-OC43, HCoV-HKU1, and an α-coronavirus, such as HCoV-NL63, HCoV-229E or PEDV, including naturally-occurring variants or mutants of any of the foregoing, or
b) Adenoviridae, preferably human Adenoviruses, such as HAdVB, HAdVC, or HAdVD;
c) human respiratory syncytial viruses (RSV), such as RSV subtype A or B; or
d) influenza viruses, such as human influenza viruses, preferably influenza virus A (IVA), such as H1N1, H3N3, or H5N1, or influenza virus B (IVB), or influenza virus C (IVC), or influenza virus D (IVD).

Specifically, a disease condition is treated which is caused by or associated with an infection by one or more Coronaviridae viruses, in particular one or more different Coronaviridae viruses.

According to a specific aspect, said Coronaviridae viruses are preferably selected from the group consisting of a β-coronavirus, such as SARS-CoV-2, MERS-CoV, SARS-CoV-1, HCoV-OC43, or HCoV-HKU1, or an α-coronavirus, such as Humane Coronavirus NL63 (HCoV-NL63, New Haven coronavirus), HCoV-229E or Porcine epidemic diarrhea virus (PEDV), including naturally-occurring variants or mutants of any of the foregoing.

Specifically, said one or more different Coronaviridae viruses referred to herein are naturally-occurring SARS-CoV-2 variants or mutants, in particular those that comprise one or more mutations of the spike protein (SARS-CoV-2 S-protein), such as any one or more of the following mutations: K417N, L452R, N501Y, D614G, P681H, P681R, E484K, E484Q, or 69/70 deletion.

Specifically, the spike protein comprises or consists of the amino acid sequence identified as SEQ ID NO:4 (sequence provided in FIG. 5, NCBI accession number QII57161.1, SARS-CoV-2, S-protein).

Preferably said one or more different Coronaviridae viruses are naturally-occurring SARS-CoV-2 variants or mutants selected from the group consisting of the UK (B1.1.7) variant, the South African (B.1.351) variant, the Brazilian (P.1) variant, the Indian (B.1.617) variant and the Bengal (B.1.618) variant.

The preparations, methods and uses described herein are specifically comprising an azelastine compound in an antiviral effective amount. Such antiviral effective amount may target one specific virus or more than one different viruses, virus mutants or virus variants, such as further described herein.

The target virus of an antiviral effect is particularly understood as the virus which is (directly or indirectly) related to the indication for the treatment described herein, in particular the treatment for prophylaxis or therapy of a disease condition or disease that is caused or otherwise associated by such target virus.

Specifically, the target of the preparations, methods and uses described herein, and in particular the target of an antiviral effect described herein, can be any one or more different virus species, virus mutants or virus variants e.g., 1, 2, 3, 4, 5, 6, 7, 8, 9, or 10 different virus species, mutants or variants.

Specifically, the target can be any two or more viruses e.g., 2, 3, 4, 5, 6, 7, 8, 9, or 10 different virus species, virus mutants or virus variants, wherein at least 2, 3, or 4 of the viruses are of different virus families, such as selected from the families:

a) Coronaviridae (β-coronavirus, such as SARS-CoV-2, MERS-CoV, SARS-CoV-1, HCoV-OC43, HCoV-HKU1; or α-coronavirus, such as HCoV-NL63, HCoV-229E or PEDV, including naturally-occurring variants or mutants of any of the foregoing);

b) Adenoviridae (such as Adenoviruses or human Adenoviruses e.g., HAdVB, HAdVC, or HAdVD);

c) Paramyxoviridae (such as RSV or human RSV e.g., hRSV subtype A or B); or d) Orthomyxoviridae (such as influenza viruses or human influenza viruses, preferably influenza virus A (IVA), such as H1N1, H3N3, or H5N1, or influenza virus B (IVB), or influenza virus C (IVC), or influenza virus D (IVD)).

Specifically, such viruses listed in a) to d) above are herein referred to as exemplary "respiratory viruses".

According to a specific example, the target can be at least one virus selected from a) and at least one virus selected from b), c), or d). Specifically, the target can be at least one β-coronavirus, such as a SARS virus, in particular SARS-CoV-2, and at least one influenza virus.

Specifically, the target can be at least one β-coronavirus, such as a SARS virus, in particular SARS-CoV-2, and at least one Adenovirus HAdVB, HAdVC, or HAdVD.

Specifically, the target can be at least one β-coronavirus, such as a SARS virus, in particular SARS-CoV-2, and at least one hRSV subtype A or B.

According to a specific example, the target can be at least one virus selected from d) and at least one virus selected from a), b), or c).

Specifically, the target can be at least one influenza viruses or human influenza viruses, and at least one Adenovirus HAdVB, HAdVC, or HAdVD.

Specifically, the target can be at least one influenza viruses or human influenza viruses, and at least one hRSV subtype A or B.

According to a specific example, the target can be at least one virus selected from b) and at least one virus selected from a), c), or d).

Specifically, the target can be at least one Adenovirus HAdVB, HAdVC, or HAdVD, and at least one hRSV subtype A or B.

According to a specific example, the target can be at least one virus selected from a) and at least one virus selected from b), and optionally at least one virus selected from c), or d). Specifically, the target can be at least one β-coronavirus, such as a SARS virus, in particular SARS-CoV-2, and at least one influenza virus, and optionally at least one one Adenovirus HAdVB, HAdVC, or HAdVD, and/or at least one hRSV subtype A or B.

The invention further provides for an azelastine compound (as further described herein) in an antiviral effective amount for use as an antiviral substance in a pharmaceutical preparation for the prophylactic or therapeutic treatment of a disease condition caused by or associated with an infection by one or more different viruses which are Coronaviridae viruses, preferably selected from the group consisting of a β-coronavirus, such as SARS-CoV-2, MERS-CoV, SARS-CoV-1, HCoV-OC43, or HCoV-HKU1, or an α-coronavirus, such as HCoV-NL63, HCoV-229E or PEDV, including naturally-occurring variants or mutants of any of the foregoing, for example, any one or more of the naturally-occurring SARS-CoV-2 variants or mutants referred to herein, preferably selected from the group consisting of the UK (B1.1.7) variant, the SA (B.1.351) variant, the Brazilian (P.1) variant, the Indian (B.1.617) variant and the Bengal (B.1.618) variant.

Specifically, the disease condition associated with or caused by a target virus, or a respiratory virus described herein, in particular wherein the target virus is a virus of the Coronaviridae, Adenoviridae, Paramyxoviridae, or Orthomyxoviridae family, is common cold, infection of the nose, sinusitis, throat and larynx, bronchiolitis, diarrhea, rash on skin, or pneumonia, acute respiratory distress syndrome (ARDS). Specifically, a disease condition can be a symptom associated with any one or more of the foregoing. Specifically, a symptom to be treated can be any of coughing, sore throat, runny nose, sneezing, headache, and fever.

According to a specific aspect, the antiviral effective amount is effective in preventing infection of susceptible cells by the virus, thereby treating the disease condition. Specifically, susceptible cells are within or at a biological surface or a subject.

According to a specific aspect, the antiviral effective amount is 0.1-500 μg/dose, preferably below any one of 100, 90, 80, 70, 50, 50, 40, 30, 20, 10, 9, 8, 7, 6, 5, 4, 3, 2, 1.9, 1.8, 1.7, 1.6, 1.5, 1.4, 1.3, 1.2, 1.1 or 1 μg/dose. Specifically, the number of doses is up to 1 to 10 per day.

According to a specific aspect, the antiviral effective amount is 15 μg-150 μg per dose, preferably less than 100 μg, or less than 50 μg.

Specifically, the antiviral effective amount may be even less, such as less than any one of 50, 40, 30, 20, 10, 9, 8, 7, 6, 5, 4, 3, 2, 1, 0.9, 0.8, 0.7, 0.6, 0.5, 0.4, 0.3, 0.2, or 0.1% of the amount ranging 15 μg-150 μg. Such lower amounts have particularly been proven to be effective with coronaviruses (or viruses of the family Coronaviridae), and/or viruses other than coronaviruses (or other than viruses of the family Coronaviridae), such as viruses of the families Adenoviridae, Paramyxoviridae, or Orthomyxoviridae.

For example, the antiviral effect targeting any of the target viruses described herein has proven to be highly effective with 0.1%, i.e. 2.39 mM) and 5× reduced (0.02%, i.e. 478 microM) dose of a commercial azelastine nasal spray preparation, thereby reducing viral load in humans.

For example, the anti-influenza virus effect has proven to be highly effective at 5× dilution (0.02%, i.e. 478 microM) and 10× dilution (0.01%, i.e. 239 microM) of a commercial azelastine preparation (being 0.1%, 2.39 mM).

For example, the anti-RSV effect has proven highly effective from a range of 0.4-6.4 microM in vitro.

According to a specific aspect, said pharmaceutical preparation is formulated for local administration, such as for topical or topical mucosal administration, preferably for application to the upper and lower respiratory tract, nasal, pulmonary, intraoral, ocular, or dermal use, or for systemic administration, preferably by intravenous, intramuscular, subcutaneous, intradermal, transdermal, or oral administration. Typically, for parenteral administration, intravenous or peroral administration is preferred.

According to a specific aspect, said pharmaceutical preparation is administered to a subject as a spray, such as a nose spray, a powder, such as an instant powder or powder for inhalation, or by a healthcare device, such as e.g., comprising a surface or fabric impregnated with the Azelastine compound for inhalation, a gel, an ointment, a cream, a foam, or a liquid solution, a lotion, a gargle solution, an aerosolized powder, an aerosolized liquid formulation, granules, capsules, drops, tablet, syrup, lozenge, an eye drop, or a preparation for infusion or injection.

Specifically, antiviral formulations and administration forms are provided, such as for veterinary and for human use. Specifically, the formulations comprise a predetermined amount of the Azelastine compound as active ingredient; e.g., as a powder or granules; as a solution or a suspension in an aqueous or non-aqueous liquid; or as an oil-in-water liquid emulsion or a water-in-oil liquid emulsion.

According to a specific aspect, the Azelastine compound is used in an antiviral effective amount to provide a peak concentration (or maximum concentration) in blood or plasma, which is about 0.01-2 μg/mL, or up to any one of 1.6, 1.5, 1.4, 1.3, 1.2, 1.1, 1.0, 0.9, 0.8, 0.7, 0.6, 0.5, 0.4, 0.3, 0.2, or 0.1 μg/mL According to a specific aspect, the Azelastine compound is used in a formulation at a concentration of 1 μM-10 mM, preferably up to any one of 1 mM, 100 μM, 90 μM, 80 μM, 70 μM, 60 μM, or 50 μM. According to a specific embodiment, the concentration is 3-50 μM.

Specifically, a liquid solution or dispersion is used for nasal administration, such as by nose drops or a nasal spray, preferably wherein the antiviral effective amount is 1-1000 μg per nostril, preferably 1-500 μg per nostril, or up to any one of 200, 190, 180, 170, 160, 150, 140, 130, 120, 110, more preferably up to 100, 90, 80, 70, 60, 50, 40, 30, 20, 10, 5, 4, 3, 2 or 1 μg per nostril.

Specifically, a dose can be administered by nasal administration which is about 2-2000 μg per dose, preferably 2-1000 μg per dose, or up to any one of 400, 380, 360, 340, 320, 300, 280, 260, 240, 220, more preferably up to 200, 180, 160, 140, 120, 100, 80, 60, 40, 20, 10, 5, 4, 3, or 2 μg per dose.

A formulation is preferably applied as a nasal spray, nasal drops, an aerosol such as an aerosolized liquid or powder e.g., as a throat spray or for intrapulmonary administration, or as eye drops.

Exemplary formulations may contain the Azelastine compound as an active ingredient in an amount of, for example, 0.001 to 2% (w/w), such as about 0.001%, 0.002%, 0.003%, 0.004%, 0.005%, 0.006%, 0.007%, 0.008%, 0.009%, 0.01%, 0.02%, 0.05%, 0.1%, 0.15%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0% (w/w).

Specifically, a volume of 100-1000 μL per dose can be applied in a sprayable formulation, e.g., up to 500 μL spray volume. According to a specific example, a nasal spray may deliver a volume of about 100-150 μL per spray. Typically, two sprays are applied per nostril one or twice daily.

When using a spray, a metered spray is preferably used to administer a certain spray volume or dose per puff.

Formulations suitable for intrapulmonary administration may have a particle size in the range of 0.1 to 500 microns, which can be administered by inhalation through the nasal passage or by inhalation through the mouth so as to reach the alveolar sacs. Suitable formulations include aqueous or oily solutions of the Azelastine compound. Formulations suitable for aerosol or dry powder administration may be prepared according to conventional methods and may be delivered with other therapeutic agents such as compounds used in the treatment or prophylaxis of lung inflammation or lung diseases.

Specifically, a liquid solution or dispersion is used for parenteral administration, such as by infusions or injections, preferably wherein the antiviral effective amount provides a dose of about 1-500 mg.

Specifically, a single loading dose of about 1-500 mg may be administered parenterally, followed by maintenance doses of about 10-200 mg, or about 100 mg, or about 200 mg, e.g., by daily administration for 1-10 days, or until a certain clinical response has been achieved.

Specifically, a tablet, gel or lozenge is used for oral administration, preferably wherein the antiviral effective amount is 1 μg-12 mg per dose, preferably up to any one of 5, 4, 3, 2, or 1 mg; or up to 100 μg per dose.

Specifically, a tablet comprising the Azelastine compound may be used which can be administered once to three times a day.

Formulations suitable for topical administration in the mouth include lozenges comprising the active ingredient in a flavored basis, such as sucrose, acacia or tragacanth, pastilles comprising the Azelastine compound in an inert basis such as gelatin and glycerin, sucrose, or acacia, or mouthwashes comprising the Azelastine compound in a suitable liquid carrier.

When formulated in a topically applied gel or ointment, the active ingredients may be employed with either a paraffinic or a water-miscible ointment base. Alternatively, active ingredients may be formulated in a cream with an oil-in-water cream base.

Formulations suitable for topical administration to the eye may include eye drops, gel or cream, wherein the Azelastine compound is dissolved or suspended in a suitable carrier, especially an aqueous solvent or oil/water emulsion.

According to specific examples, such formulations for a topical administration in the mouth, or a topically applied formulation such as a gel or ointment, may comprise the Azelastine compound in a concentration of, for example, 0.001 to 20% (w/w), such as about 0.001%, 0.002%, 0.003%, 0.004%, 0.005%, 0.006%, 0.007%, 0.008%, 0.009%, 0.01%, 0.02%, 0.05%, 0.1%, 0.15%, 0.2%, 0.3%, 0.4%, 0.5%, 0.6%, 0.7%, 0.8%, 0.9%, 1.0%, 2%, 3%, 4%, 5%, 6%, 7%, 8%, 9%, 10%, 11%, 12%, 13%, 14%, 15%, 16%, 17%, 18%, 9, or 20% (w/w).

According to a specific aspect, treatment with the Azelastine compound can be combined with a further treatment administering an Azelastine compound (which can be the same or a different compound) in another administration form. For example, treatment with an intranasal or throat spray comprising Azelastine Hydrochloride can be combined with a tablet comprising an Azelastine compound (which can be Azelastine Hydrochloride or different from Azelastine Hydrochloride).

According to a specific aspect, the Azelastine compound is administered as the sole antiviral substance, or wherein treatment is combined with a further treatment such as an additional antiviral, anti-inflammatory and/or antibiotic treatment e.g., comprising administration of one or more antiviral substances or agents, and/or one or more anti-inflammatory and/or antibiotic substances or agents, by one or more different preparations and/or one or more different routes of administration.

Specifically, the Azelastine compound can be combined with one or more additional active therapeutic agents in a unitary dosage form for simultaneous, co-administration or sequential administration to a subject. The combination therapy may e.g., be administered as a simultaneous, parallel or sequential regimen. When administered sequentially, the combination may be administered in two or more administrations.

According to a specific aspect, a subject is treated who has been infected or is at risk of being infected with said virus, preferably a human being, or a non-human mammal, such as a dog, cat, horse, camelids, cattle or pig.

Specifically, the subject is or has been exposed to a virus, or is otherwise at risk of being infected with the virus.

Specifically, the subject has a weakened immune system and is at a higher risk of developing a viral disease or increased severity of viral disease.

Specifically, the subject has been determined or diagnosed of being infected with the virus.

In specific embodiments, a subject is treated which is a diseased subject or patient suffering from Coronaviridae virus-caused disease, e.g., a SARS virus-caused disease, upon getting in contact with the pathogen, such as COVID19, or COVID19-associated pneumonia.

In further specific embodiments, a subject is treated which is a diseased subject or patient suffering from an influenza virus-caused disease, e.g., influenza.

The invention further provides for the Azelastine compound as described herein for use as an antiviral substance in a medicinal product for treating a biological surface to prevent from virus infection and/or virus spread.

According to a specific aspect, said medicinal product is formulated for topical use, preferably for application to the upper and lower respiratory tract, nasal, pulmonary, intraoral, ocular, or dermal use.

Topical application typically refers to the surface of the skin, a wound, and/or mucosal cells or tissues (e.g., alveolar, buccal, lingual, masticatory, or nasal mucosa, etc.).

According to a specific aspect, said medicinal product is used in a formulation suitably used for topical administration, in particular mucosal administration, such as a spray, solution, dispersion, dry powder, or aerosolized liquid or powder.

According to a specific aspect, the Azelastine compound is applied to a biological surface in an antiviral effective amount, preferably wherein the amount is 1 ng-1000 ng per $cm^2$, preferably 10-800 $ng/cm^2$, or up to any one of 800, 700, 600, 500, 400, 300, 200, 100, 90, 80, 70, 60, 50 $ng/cm^2$.

Any of the medicinal products suitably used for topical treatment as described herein can be used for treating the biological surface.

According to a specific aspect, the biological surface comprises or consists of a mucosal surface which is infected or at risk of being infected with said virus.

The invention further provides for the use of an Azelastine compound as described herein, as viral disinfectant, in particular suitable for treating a biological surface, or a non-biological surface, such as sanitary devices face masks, etc. Specifically, animate or non-animate surfaces can be treated using the disinfectant.

Specifically, the viral disinfectant is an antiviral preparation, such as a medicinal product.

According to specific aspect, the invention provides for an Azelastine compound as described herein, for use in preventing or treating a Coronaviridae viral infection, in particular a SARS virus infection, in a human or non-human mammal.

According to specific aspect, the invention provides for an Azelastine compound as described herein, for use in preventing or treating a Coronaviridae viral infection, in particular a SARS virus infection, in a human or non-human mammal.

According to specific aspect, the invention provides for an Azelastine compound as described herein, for use in preventing or treating an Adenoviridae viral infection, in particular a HAdVB, HAdVC, or HAdVD virus infection in a human being.

According to specific aspect, the invention provides for an Azelastine compound as described herein, for use in preventing or treating a Paramyxoviridae viral infection, in particular a human RSV virus infection, in a human being.

According to specific aspect, the invention provides for an Azelastine compound as described herein, for use in preventing or treating a Orthomyxoviridae viral infection, in particular an influenza virus infection, in a human or non-human mammal.

According to a specific aspect, a kit is provided which comprising one or more individual dosage units of the Azelastine compound as further described herein, and directions for their use in treating a Coronaviridae viral infection or a Coronaviridae virus-caused disease, in a human or non-human mammal.

According to another specific aspect, a kit is provided which comprising one or more individual dosage units of the Azelastine compound as further described herein, and directions for their use in treating an Adenoviridae viral infection, in particular a HAdVB, HAdVC, or HAdVD virus infection in a human being.

According to another specific aspect, a kit is provided which comprising one or more individual dosage units of the Azelastine compound as further described herein, and directions for their use in treating a Paramyxoviridae viral infection, in particular a human RSV virus infection, in a human being.

According to another specific aspect, a kit is provided which comprising one or more individual dosage units of the Azelastine compound as further described herein, and directions for their use in treating a Orthomyxoviridae viral infection, in particular an influenza virus infection, in a human or non-human mammal.

According to a specific aspect, the invention provides for an antiviral pharmaceutical preparation comprising the Azelastine compound as further described herein and a pharmaceutically acceptable carrier.

Specifically, the pharmaceutical preparation is provided for medical use, in particular, for use in the prophylactic or therapeutic treatment of a disease condition caused by Coronaviridae virus such as COVID19.

Specifically, the pharmaceutical preparation is provided for medical use, in particular, for use in the prophylactic or therapeutic treatment of a disease condition caused by a Coronaviridae virus and/or an Adenoviridae virus and/or a Paramyxoviridae virus and/or a Orthomyxoviridae virus.

According to a specific aspect, the invention further provides for methods of treating a subject being infected or at risk of being infected with one or more different viruses such as one or more of Coronaviridae viruses and/or Adenoviridae viruses and/or Paramyxoviridae viruses and/or Orthomyxoviridae viruses, comprising administering an antiviral effective amount of the Azelastine compound, and respective medicinal products or pharmaceutical preparations as further described herein.

According to a further specific aspect, the invention provides for an antiviral preparation of the Azelastine compound as described herein (such as a medicinal product, pharmaceutical preparation or disinfectant) and methods of producing such antiviral preparation comprising formulating an antiviral effective amount of the Azelastine compound with a pharmaceutically acceptable carrier to produce an antiviral preparation, in particular a medicinal product or pharmaceutical preparation.

The topical administration of any of the antiviral preparations as described herein (such as a medicinal product, pharmaceutical preparation or disinfectant) to a biological surface is preferably such that upon a certain contact time of e.g. 10 minutes to 24 hours, and/or up to 24, 18, 12, 6, 5, 4, 3, 2, or 1 hour(s), contacting results in at least a 0.5-fold (by half) reduction, or 1-log, 2-log, 3-log, 4-log, 5-log reduction in a virus on said surface.

FIGURES

Figure 1B:
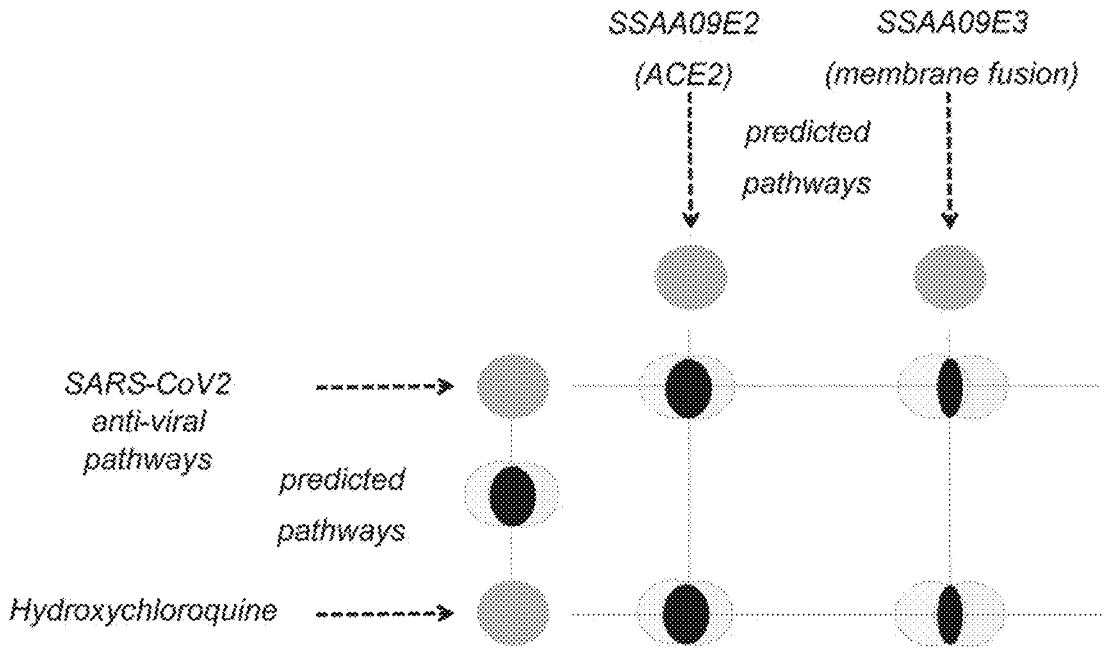

FIG. 1A shows the illustration of the Shannon entropy approach for the identification of drug homologs with matching pathway profiles. FIG. 1B shows the identification of SARS-COV-2 relevant pathways. Pathway profiles were calculated for Hydroxychloroquine and SARS inhibitors with well-defined mechanisms and mode of actions: SSAA09E2, small molecule ACE2 inhibitor and SSAA09E3, a general inhibitor of virus host membrane fusion.

Figure 2:
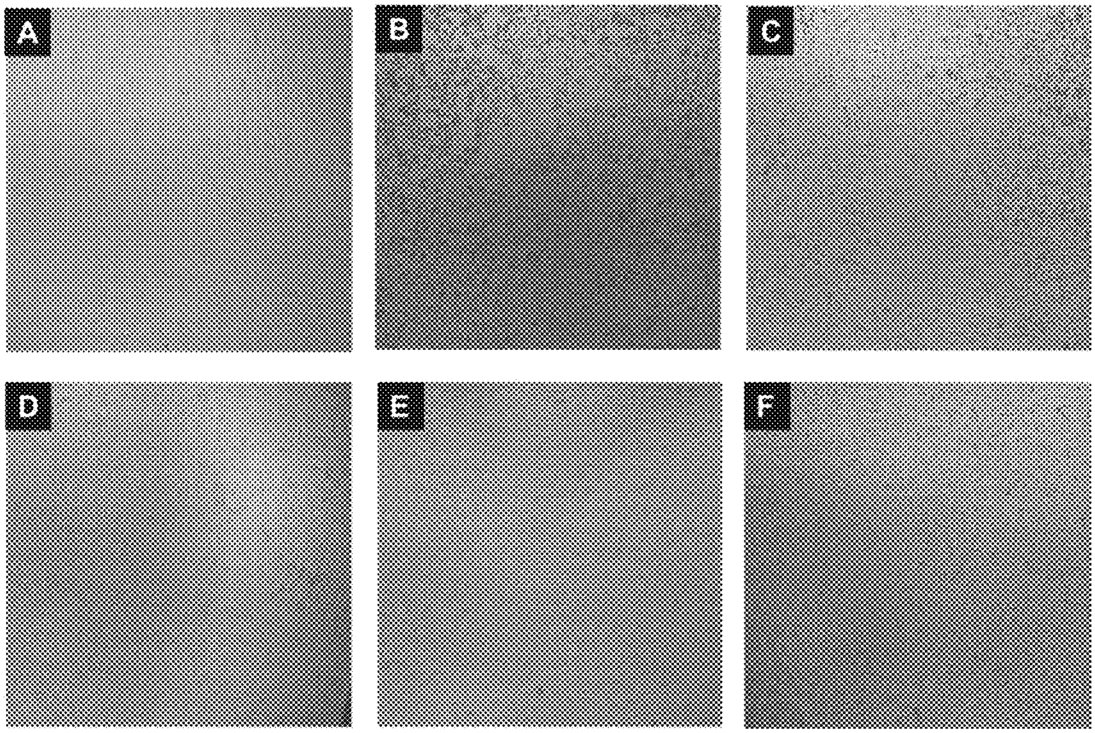

FIG. 2 shows the prevention of the cytopathic effect of SARS-COV-2 caused to Vero E6 cells based on phasis contrast microscopic pictures. A: Uninfected (control) culture; B: Cells infected with SARS-COV-2; C-F: Cells infected with SARS-COV-2 in the presence of increasing concentrations of Azelastine-HCl: 3.125, 6.25, 12.5 and 25 µM. Cells were infected with MOI 0.1 SARS-Co-V2 virus for 30 min, then the culture medium was removed and replaced with fresh culture medium without virus (but containing Azelastine), and microscopic pictures taken 48 hours post infection.

Figure 3:
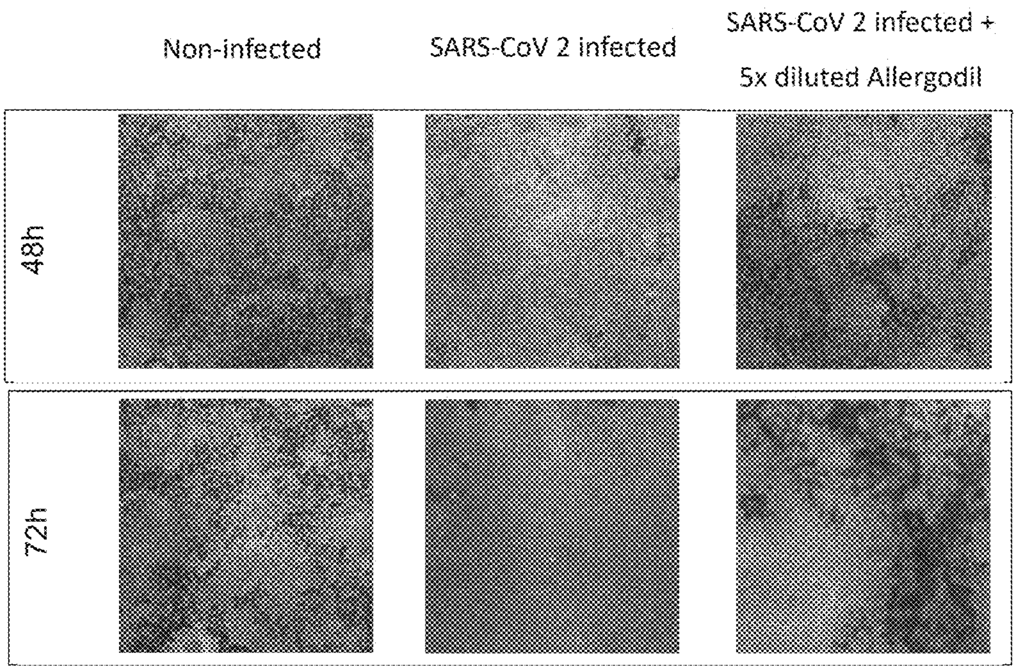

FIG. 3 shows the reduction of the cytopathic effect of SARS-CoV-2 on reconstituted human nasal tissue (MucilAir). The human nasal tissue was infected with SARS-CoV-2 and subsequently treated with 5-fold diluted 0.1% Azelastine-HCl-containing nasal spray solution for 20 min in every 24 hours for 3 days. Figure shows the low resolution microscopic image of the human nasal tissue after 48 and 72 hours post-infection. Mucin production (as the sign of intact tissue function) is demonstrated as the presence of dark spots on the tissue.

Figure 4A:
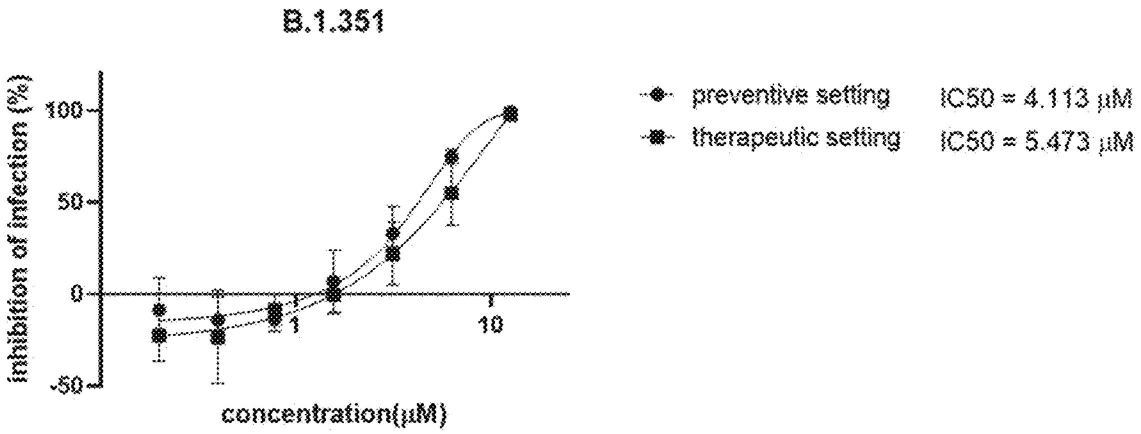
Figure 4B:
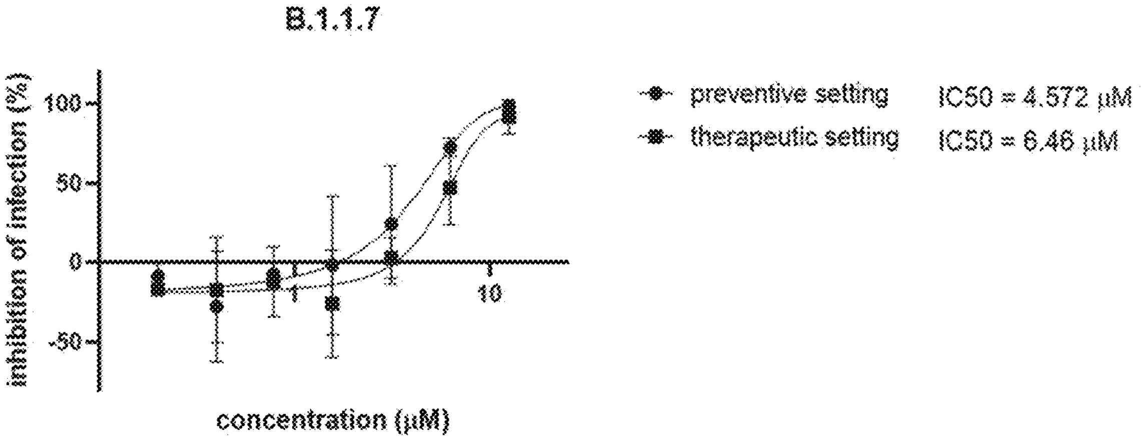

FIGS. 4A and 4B (In vitro inhibition of SARS-COV-2 B.1.351 and B.1.1.7 infection by azelastine) shows the effect of azelastine inhibiting infection of Vero-TMPRSS2/ACE2 cells with SARS-COV-2 B.1.351 (FIG. 4A) or B.1.1.7 (FIG. 4B). Cells were infected with MOI 0.01 SARS-COV-2 virus for 30 min, azelastine was added to the infected cells either right before the infection (preventive setting) or 30 minutes after infection (therapeutic setting). 48 h post-infection viral copy number was determined by quantitative PCR. Inhibition of infection is expressed as viral copy number relative to the virus only wells (no azelastine treatment). Graphs show mean and standard deviation calculated from 9 (FIG. 4A) or 6 (FIG. 4B) individual values. The azelastine concentration inhibiting 50% of the infection (EC50) was calculated with nonlinear regression (log (agonist) vs. normalized response—variable slope) using GraphPad Prism 8.4.3.

FIG. 5: SEQ ID NO:4 (NCBI accession number QII57161.1, SARS-CoV-2, S-protein).

Figure 6:
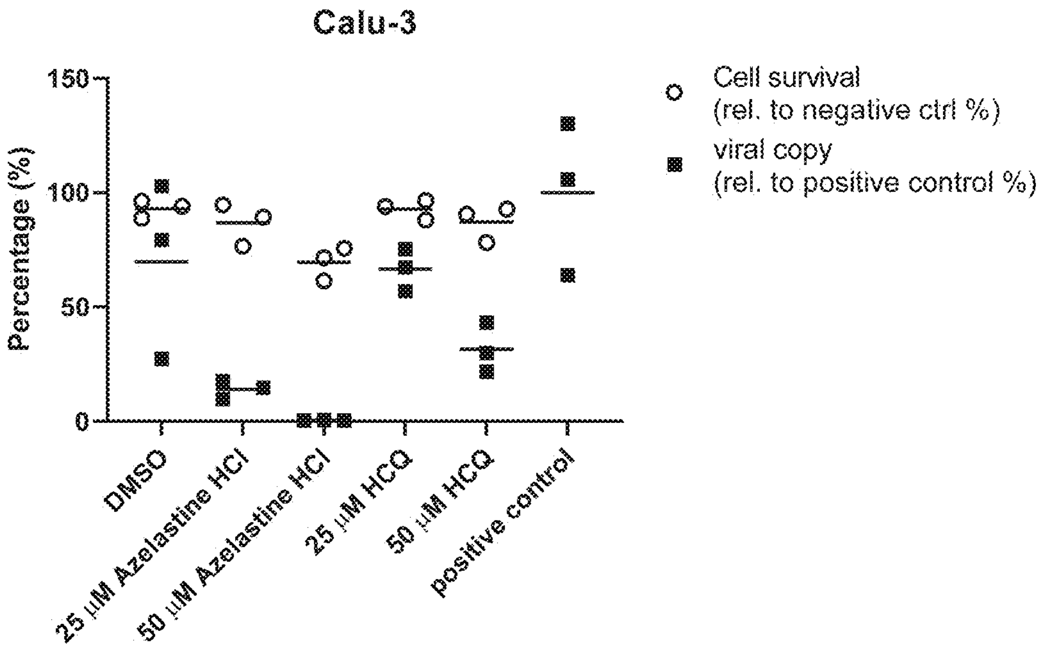

FIG. 6: Antiviral effect of Azelastine at 2 different concentrations as determined in Calu-3 human cells infected by SARS-CoV-2 at a MOI of 0.01, as well as cytotoxicity of the same concentrations of the compound measured on identical cells without viral infection. Graph shows mean results of triplicates from one representative experiment.

Figure 7:
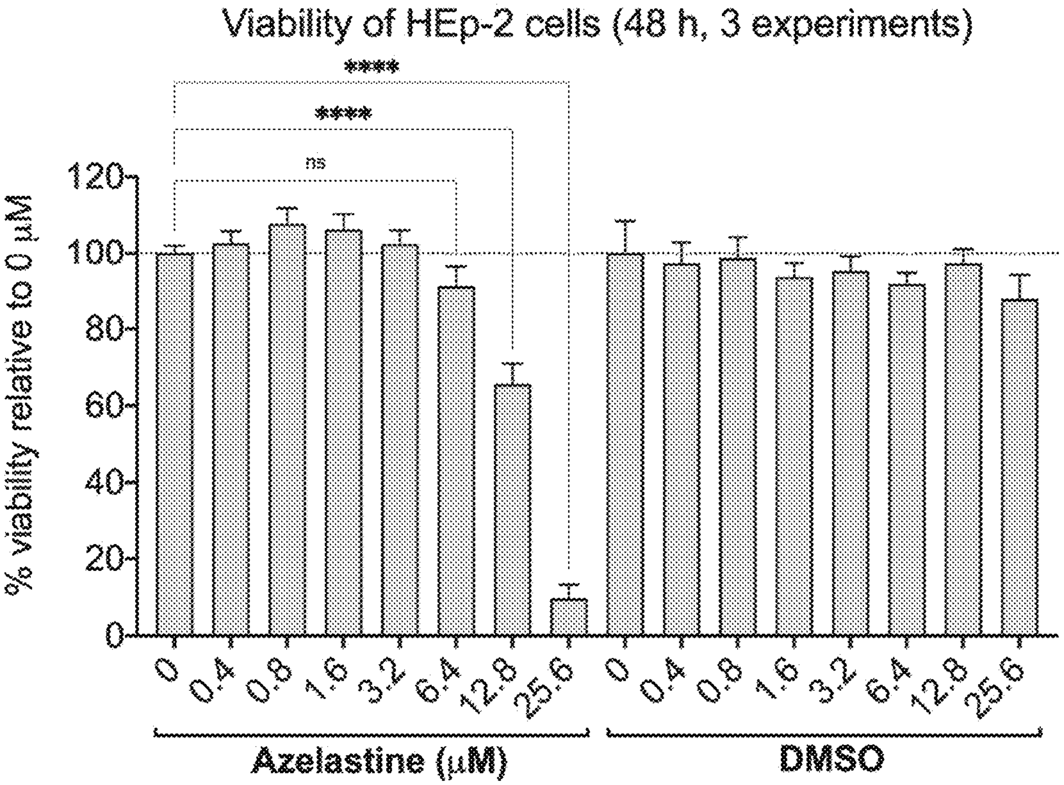
Figure 8A:
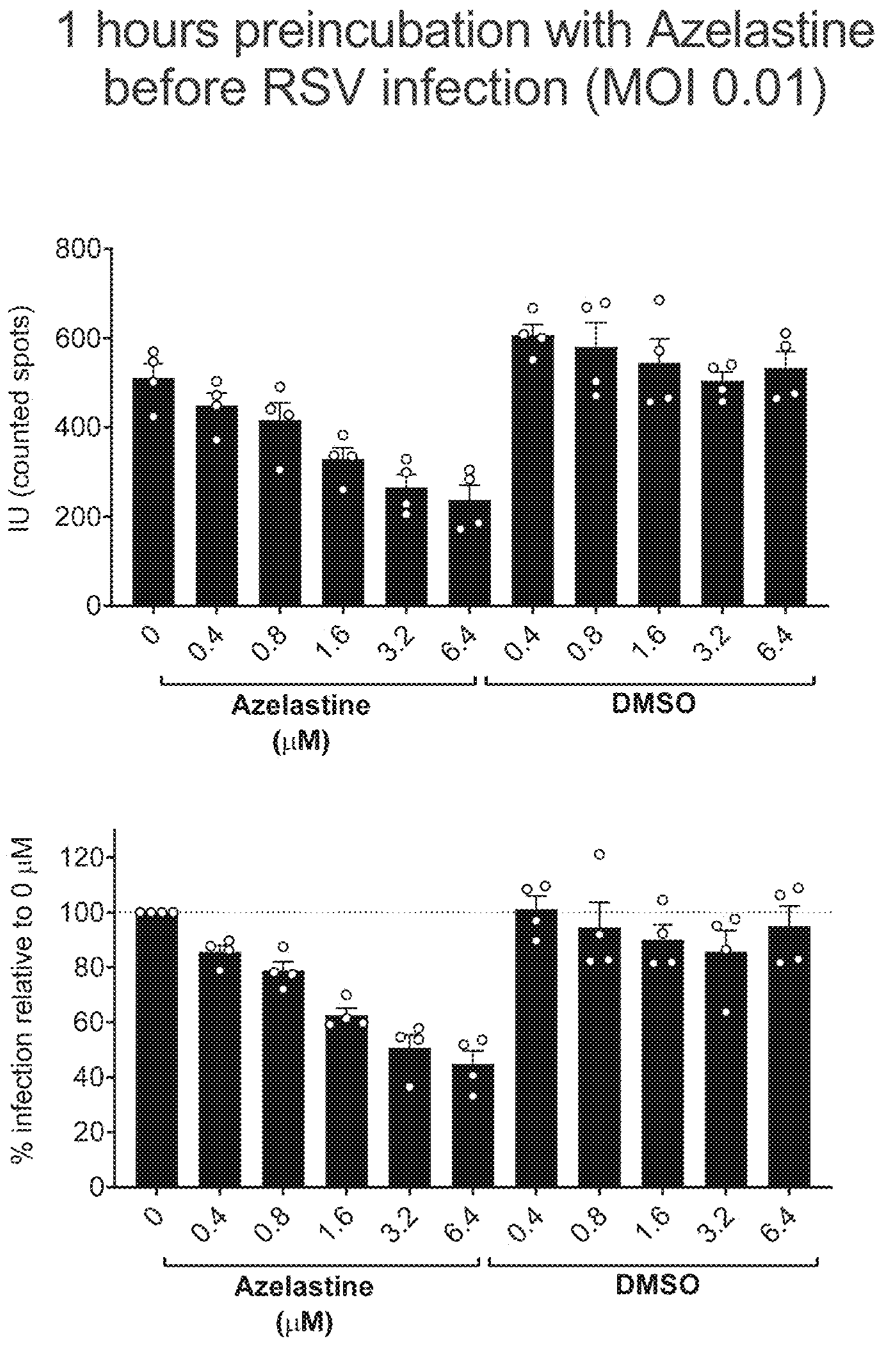
Figure 8B:
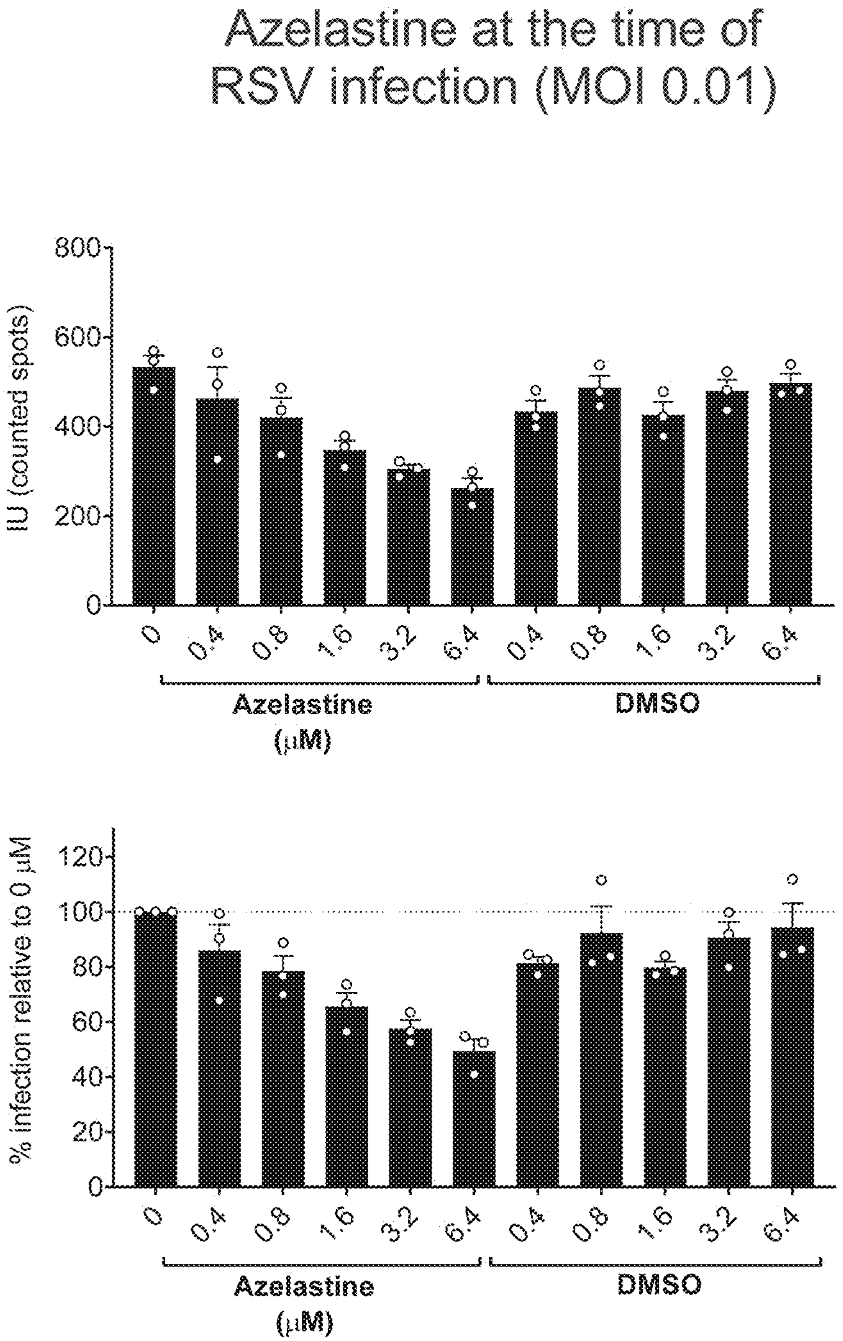
Figure 8C:
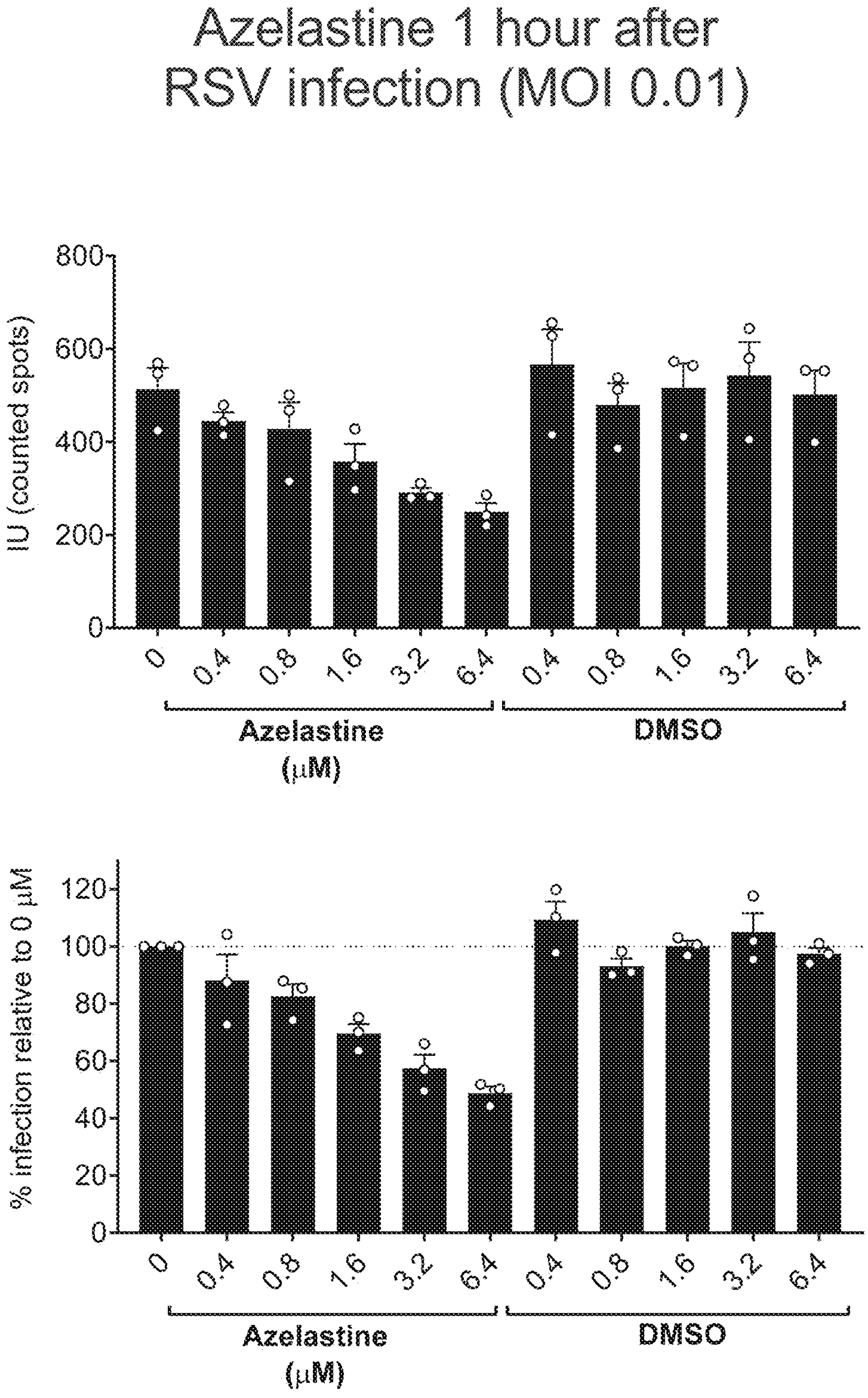

FIG. 7: Viability of non-infected Hep-2 cells treated with the indicated final concentration range of azelastine-HCl and the correspondingly diluted vehicle, DMSO for 48 h. Mean and SEM were calculated from 3 independent experiments. Threshold for statistically significant difference was $P<0.05$. **$P<0.0001$ FIGS. 8A, 8B, and 8C: Antiviral effect of azelastine-HCl at the indicated final concentration range on RSV infection of HEp-2 cells. Azelastine-HCl was applied prior to (FIG. 8A), simultaneously (FIG. 8B), or after (FIG. 8**C) virus infection and replication was assessed by visualizing RSV infected cells as described in the text. DMSO, the solvent of the azelastine-HCl stock was diluted correspondingly to serve as control. Experiments were repeated twice with duplicates. Bars represent mean with standard error of the mean as error bars.

Figure 9:
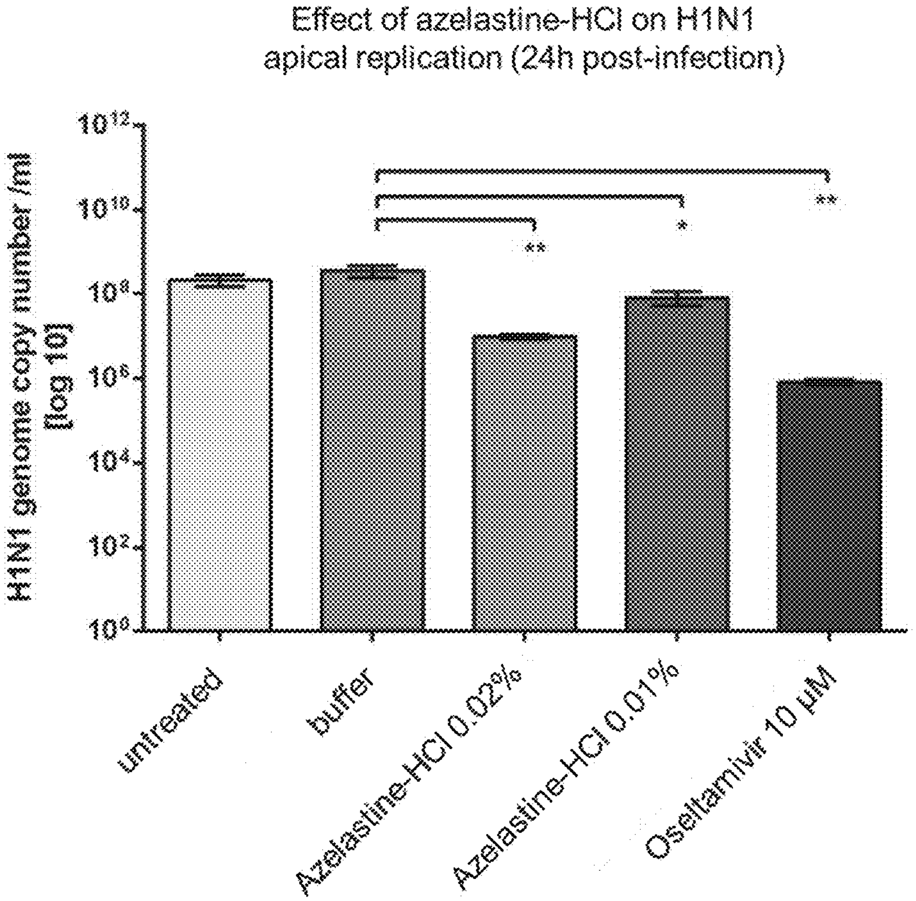
Figure 10A:
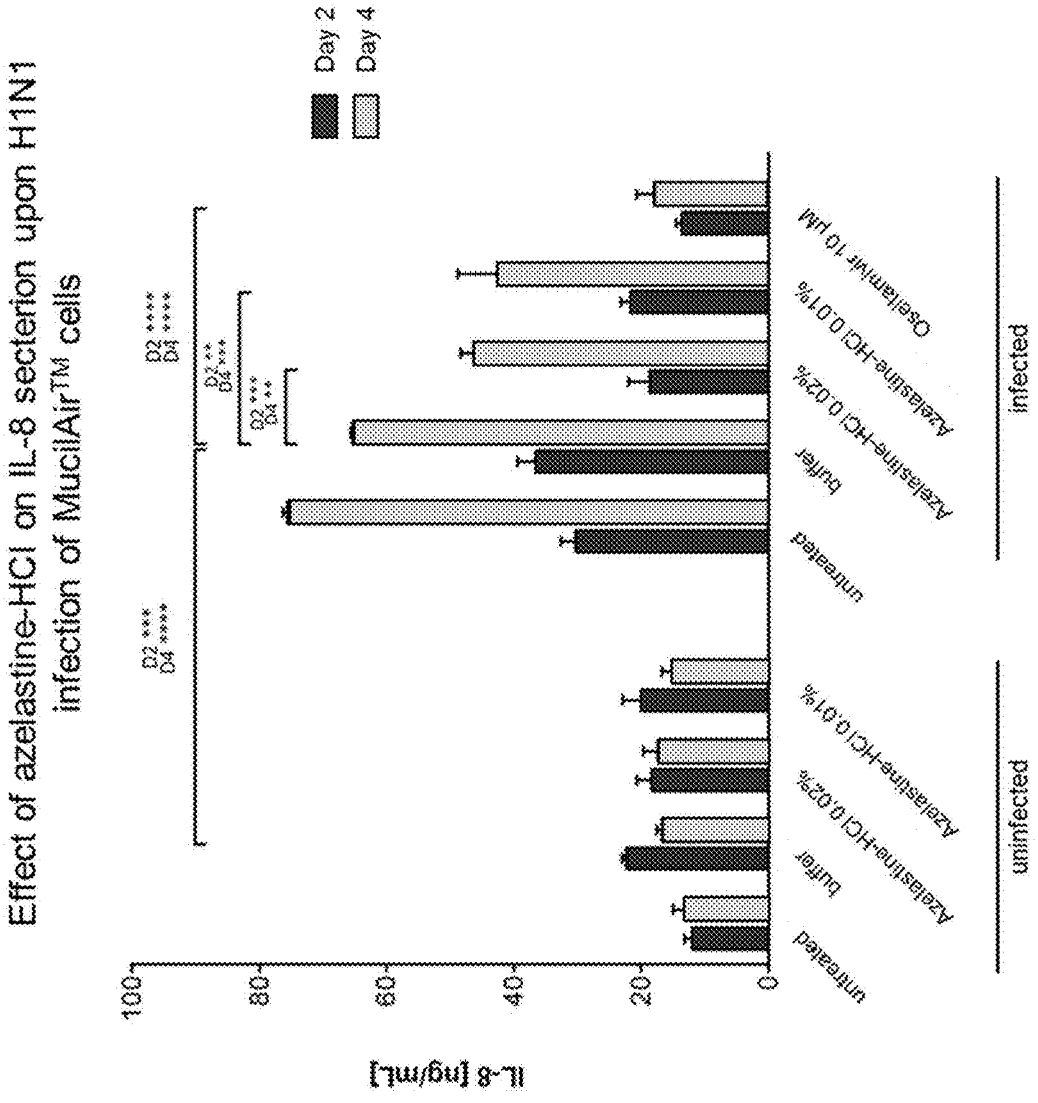
Figure 10B:
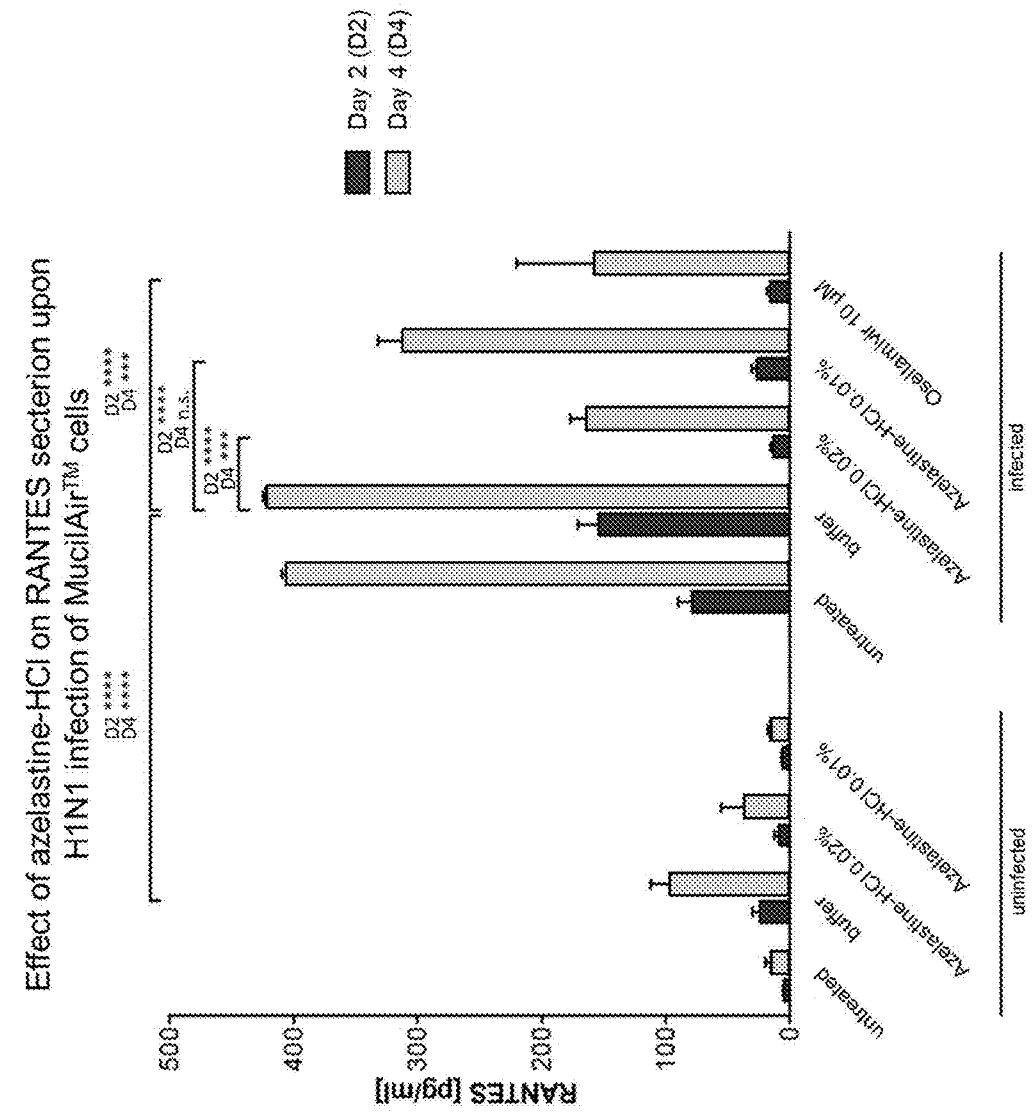

FIG. 9 Influence of two different concentrations of azelastine-HCl as well as oseltamivir on the viral copy numbers obtained from apical washes of reconstituted nasal tissues at 24 h after infection by influenza virus H1N1. Statistically significant differences are marked by asterisks. Graph show mean results of triplicates from one representative experiment. *$P<0.05$, $P<0.01$ FIGS. 10A and 10B: Effect of two different concentrations of azelastine as well as oseltamivir on the levels of IL-8 (FIG. 10A) and RANTES (FIG. 10B) secreted by reconstituted nasal tissues that had been infected by influenza virus H1N1. Statistically significant differences are marked by asterisks. Graph show mean values of the results of triplicates from one representative experiment. $P<0.01$; *$P<0.001$; **$P<0.0001$

DETAILED DESCRIPTION OF THE INVENTION

The terms “comprise”, “contain”, “have” and “include” as used herein can be used synonymously and shall be understood as an open definition, allowing further members or parts or elements. “Consisting” is considered as a closest definition without further elements of the consisting definition feature. Thus “comprising” is broader and contains the “consisting” definition.

The term “about” as used herein refers to the same value or a value differing by +/−10% or +/−5% of the given value.

The term “Azelastine compound” as used herein shall refer to Azelastine, or a salt thereof.

The molecular formula of Azelastine is $C_{22}H_{24}ClN_3O$ with the following chemical structure (I):

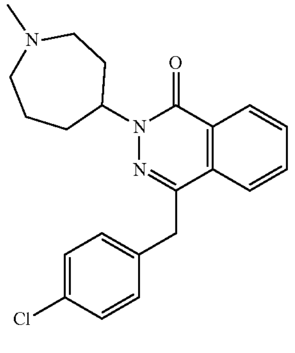 [SMILES: CN1CCCC(n2nc(Cc3ccc(Cl)cc3)c3ccccc3c2=O)CC1]

IUPAC name: 4-[(4-chlorophenyl)methyl]-2-(1-methylazepan-4-yl)phthalazin-1-one.

CAS number: 58581-89-8.

The Azelastine salt is preferably a pharmaceutically acceptable salt, such as for example a hydrochloride.

Azelastine hydrochloride is the hydrochloride salt form of azelastine, and used as an anti-histamine drug compound formulated as a metered-spray solution for intranasal administration. Commercial products comprising Azelastine hydrochloride are provided as nasal spray containing 0.1% or 0.15% Azelastine hydrochloride USP in an aqueous solution at pH 6.8±0.3.

Azelastine hydrochloride occurs as a white or almost white, crystalline powder. It is sparingly soluble in water and soluble in ethanol and dichloromethane.

Molecular formula: $C_{22}H_{25}Cl_2N_3O$.

IUPAC name: 4-[(4-chlorophenylmethyl]-2-(1-methylazepan-4-yl)phthalazin-1-one; hydrochloride.

CAS numbers: 58581-89-8; 37932-96-0; 79307-93-0.

The choice of an Azelastine salt is determined primarily by how acid or basic the chemical is (the pH), the safety of the ionized form, the intended use of the drug, how the drug is given (for example, by mouth, injection, or on the skin), and the type of dosage form (such as tablet, capsule, or liquid).

The term "pharmaceutically acceptable" also referred to as "pharmacologically acceptable" means compatible with the treatment of animals, in particular, humans. The term pharmacologically acceptable salt includes both pharmacologically acceptable acid addition salts and pharmacologically acceptable basic addition salts.

The term "pharmacologically acceptable acid addition salt" as used herein means any non-toxic organic or inorganic salt of any base compound of the disclosure, or any of its intermediates. Basic compounds of the disclosure that may form an acid addition salt include, for example, compounds that contain a basic nitrogen atom. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono-, di- or the triacid salts can be formed, and such salts may exist in either a hydrated, solvated or substantially anhydrous form. In general, the acid addition salts of the compounds of the disclosure are more soluble in water and various hydrophilic organic solvents, and generally demonstrate higher melting points in comparison to their free base forms. The selection of the appropriate salt will be known to one skilled in the art. Other non-pharmacologically acceptable acid addition salts, e.g. oxalates, may be used, for example, in the isolation of the compounds of the disclosure, for laboratory use, or for subsequent conversion to a pharmacologically acceptable acid addition salt.

The term "pharmacologically acceptable basic salt" as used herein means any non-toxic organic or inorganic basic addition salt of any acid compound of the invention, or any of its intermediates, which are suitable for or compatible with the treatment of animals, in particular humans. Acidic compounds of the invention that may form a basic addition salt include, for example compounds that contain carboxylic acid, sulfonic acid, sulfinic acid, sulfonamide, N-unsubstituted tetrazole, phosphoric acid ester, or sulfuric acid ester. Illustrative inorganic bases which form suitable salts include lithium, sodium, potassium, calcium, magnesium, or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmacologically acceptable basic addition salts, may be used, for example, in the isolation of the compounds of the invention, for laboratory use, or for subsequent conversion to a pharmacologically acceptable basic addition salt. The formation of a desired compound salt is achieved using standard techniques. For example, the neutral compound is treated with a base in a suitable solvent and the formed salt is isolated by filtration, extraction or any other suitable method.

The term "antiviral" as used herein shall refer to any substance, drug or preparation, that effects the biology of a virus and attenuates or inhibits viral attachment, entry, replication, shedding, latency or a combination thereof, resulting in reduction of viral load or infectivity. The terms "attenuating," "inhibiting," "reducing," or "prevention," or any variation of these terms, when used in the claims and/or the specification includes any measurable decrease or complete inhibition to achieve a desired result, e.g., reduction in the risk of viral infection (pre-exposure), or reduction of post-exposure viral survival, load, or growth.

Exemplary antiviral preparations described herein are medicinal products, pharmaceutical preparations, or disinfectants, for in vivo, ex vivo or in vitro use.

The term "biological surface" as used herein shall refer to a surface comprising viable cells, such as mammalian (human or non-human animal) cells, including e.g., a biological tissue surface, such as a surface or epithelial or dermal tissue (e.g. skin), mucosal tissue, or membrane tissue.

The term "effective amount" with respect to an antiviral effect as used herein, shall refer to an amount (in particular a predetermined amount) that has a proven antiviral effect. The amount is typically a quantity or activity sufficient to, when applied to a surface or administered to a subject effect beneficial of desired results, including antiviral or clinical results, and, as such, an effective amount or synonym thereof depends upon the context in which it is being applied.

An effective amount of a pharmaceutical preparation or drug is intended to mean that amount of a compound that is sufficient to treat, prevent or inhibit a disease, disease condition or disorder. Such an effective dose specifically refers to that amount of the compound sufficient to result in healing, prevention or amelioration of conditions related to diseases or disorders described herein.

In the context of disease, effective amounts (in particular prophylactically or therapeutically effective amounts) of an Azelastine compound as described herein are specifically used to treat, modulate, attenuate, reverse, or affect a disease or condition that benefits from its antiviral effect. The amount of the compound that will correspond to such an effective amount will vary depending on various factors, such as the given drug or compound, the formulation, the route of administration, the type of disease or disorder, the identity of the subject or host being treated, the assessment of the medical situations and other relevant factors, but can nevertheless be routinely determined by one skilled in the art.

A treatment or prevention regime of a subject with an effective amount of the Azelastine compound described herein may consist of a single application or administration, or alternatively comprise a series of applications and administrations, respectively. For example, the Azelastine compound may be used at least once a month, or at least once a week, or at least once a day. However, in certain cases of an acute phase, e.g. upon suspected or confirmed exposure to a virus, or after virus infection has been determined, the Azelastine compound may be used more frequently e.g., 1-10 times a day.

Specifically, a combination therapy is provided which includes treatment with the preparation described herein and standard therapy of a Coronaviridae virus-caused disease and/or standard therapy of a disease caused by any of the other target viruses.

Doses may be applied in combination with other active agents such as antiviral agents, anti-inflammatory drugs or antibiotics, e.g. upon the subject's risk of viral spread, so to prevent a pathogen associated reaction.

Treatment can be combined with an antiviral, anti-inflammatory or antibiotic treatment, preferably wherein a pharmaceutical preparation is administered before, during (e.g., by co-administration or in parallel), or after said antiviral, anti-inflammatory or antibiotic treatment.

Specifically, the Azelastine compound described herein can be combined with an additional antiviral agent, which can be an Azelastine compound, e.g. the same of a different compound. Specific embodiments refer to further antiviral agents selected from an ACE2 inhibitor, a viral protein M2 ion channel inhibitor, a neuraminidase inhibitor, an RNA replication and translation inhibitor and a polymerase inhibitor. The antiviral agent may be amantadine or rimantadine. Specifically, the antiviral agent may be oseltamivir, zanamivir, peramivir, ribavirin, lopinavir, or ritonavir. Specific further antiviral examples are those suitably used for biological surface treatment such as carrageenan, or those currently under investigation for treating SARS-Cov2 infections, such as hydroxychloroquine, or remdesivir.

Specifically, the Azelastine compound is combined with an anti-inflammatory agent such as standard steroidal anti-inflammatory drugs, glucocorticoids and nonsteroidal anti-inflammatory drugs (NSAID's). Suitable NSAID's include, but are not limited to ibuprofen, naproxen, fenoprofen, ketoprofen, flurbiprofen, oxaprozin, indomethacin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, tolfenamic acid and celecoxib. Suitable steroidal anti-inflammatory agents include, but are not limited to, corticosteroids such as synthetic glucocorticoids. Specific examples are fluticasone, COX-2 inhibitors, ibuprofen, hydroxychloroquine, heparin, LMW heparin, hirudine, or immunosuppressants, such as azathioprine, cyclosporin A, or cyclophosphamide.

Specifically, the Azelastine compound is combined with an antibiotic such as a beta lactam antibiotic, an aminoglycoside antibiotic, an ansamycin, a carbacephem, a carbapenem, a cephalosporin, a glycopeptide, a lincosamide, a lipopeptide, a macrolide, a monobactam, a nitrofuran, an oxazolidinone, a polypeptide, a sulfonamide, Clofazimine, Dapsone, Capreomycin, Cycloserine, Ethambutol, Ethionamide, Isoniazid, Pyrazinamide, Rifampicin, Rifabutin, Rifapentine, Streptomycin, Arsphenamine, Chloramphenicol, Fosfomycin, Mupirocin, Platensimycin, Quinupristin/Dalfopristin, Thiamphenicol, Tigecycline, Tinidazole, Trimethoprim, Teixobactin, Malacidins, Halicin, clindamycin, vancomycin, metronidazole, fusidic acid, thiopeptides, fidaxomicin, quinolones, tetracyclins, omadacycline, rifamycin, kibdelomycin, oxazolidinone, ketolides, thiazolides, amixicile, teicoplanin, ramoplanin, oritavancin, lantibiotics, capuramycin, surotomycin, thuricin, endolysin, avidocin CD, cadazolid, ramizol, defensins, ridinilazole, medium-chain fatty acids, phages, berberine, lactoferrin.

Specifically, treatment with the Azelastine compound described herein can be combined with a treatment administering at least one other therapeutic agent selected from the group consisting of a corticosteroid, an anti-inflammatory signal transduction modulator, a 2-adrenoreceptor agonist bronchodilator, an anticholinergic, a mucolytic agent, hypertonic saline and other drugs for treating a Coronaviridae virus infections and/or infections by any of the other target viruses described herein; or mixtures thereof. Specific pharmaceutical compositions may particularly include one or more anti-inflammatory agents, and/or analgesics, PPAR-γ agonists and immune response modulators.

The length of the treatment period depends on a variety of factors, such as the severity of the disease, either acute or chronic disease, the age of the patient, and the concentration of the Azelastine compound. It will also be appreciated that the effective dosage used for the treatment or prophylaxis may increase or decrease over the course of a particular treatment or prophylaxis regime. Changes in dosage may result and become apparent by standard diagnostic assays known in the art.

According to a specific aspect, a medicinal product or pharmaceutical composition described herein contains an effective amount of the Azelastine compound as defined herein. The preparation described herein may be provided for single or multiple dosage use.

Unit-dose or multi-dose containers may be used, for example, sealed ampoules and vials, or multi-use sprays, and may be stored comprising a liquid or dry phase, e.g., in a freeze-dried (lyophilized) condition requiring only the addition of the sterile liquid carrier, for example water for injection, immediately prior to use. Preferred unit dosage formulations are those containing a daily dose or unit daily sub-dose, or multiple doses, of the Azelastine compound.

The term "single-dose" as used herein is understood in the following way. A single-dose or amount for single-use is the amount intended for administration that is meant for use in a single subject, such as a patient, either human or animal for a single case/procedure/administration. Packages comprising the single-dose are typically labelled as such by the manufacturer. The single-dose amount is specifically understood as a daily dose for an individual, like a child or adult, to provide an effective amount.

The medicinal product or pharmaceutical composition described herein is specifically provided as human or veterinary medicinal product or pharmaceutical composition. Medicinal products are understood as substances that are used to treat diseases, to relieve complaints, or to prevent such diseases or complaints in the first place. This definition applies regardless of whether the medicinal product is administered to humans or to animals. The substances can act both within or on the body.

The medicinal product or pharmaceutical composition described herein preferably contains one or more pharmaceutically acceptable auxiliaries and is in a pharmaceutical form which allows the active pharmaceutical compound to be administered with high bioavailability. Suitable auxiliaries may be, for example, based on cyclodextrins. Suitable formulations might for example incorporate synthetic polymeric nanoparticles formed of a polymer selected from the group consisting of acrylates, methacrylates, cyanoacrylates, acrylamides, polylactates, polyglycolates, polyanhydrates, polyorthoesters, gelatin, albumin, polystyrenes, polyvinyls, polyacrolein, polyglutaraldehyde and derivatives, copolymers and mixtures thereof.

Specific medicinal products or pharmaceutical compositions described herein comprise the Azelastine compound and a pharmaceutically acceptable carrier or excipient. A "pharmaceutically acceptable carrier" refers to an ingredient in a formulation for medicinal or medical use, other than an active ingredient, which is nontoxic to a subject. A pharmaceutically acceptable carrier includes, but is not limited to, a buffer, excipient, stabilizer, or preservative, and in particular saline, phosphate buffered saline, dextrose, glycerol, ethanol, and the like.

The Azelastine compound as used herein can be formulated with conventional carriers and excipients, which will be selected in accord with ordinary practice.

Pharmaceutically acceptable carriers generally include any and all suitable solvents, dispersion media, coatings, antiviral, antibacterial and antifungal agents, isotonic and absorption delaying agents, and the like that are physiologically compatible with an antiviral small molecule compound or related composition or combination preparation described herein.

According to a specific aspect, the Azelastine compound can be combined with one or more carriers appropriate a desired route of administration. The Azelastine compound may be e.g., admixed with any of lactose, sucrose, starch, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, polyvinyl alcohol, and optionally further tableted or encapsulated for conventional administration. Alternatively, the Azelastine compound may be dispersed or dissolved in saline, water, polyethylene glycol, propylene glycol, carboxymethyl cellulose colloidal solutions, ethanol, corn oil, peanut oil, cotton seed oil, sesame oil, tragacanth gum, and/or various buffers. Other carriers, adjuvants, and modes of administration are well known in the pharmaceutical arts. A carrier may include a controlled release material or time delay material, such as glyceryl monostearate or glyceryl distearate alone or with a wax, or other materials well-known in the art.

Compounds as described herein may be provided in controlled release pharmaceutical ("controlled release formulations") in which the release of the Azelastine compound is controlled and regulated to allow less frequency dosing or to improve the pharmacokinetic or toxicity profile of a given active ingredient.

Pharmaceutical compositions may also be coated by conventional methods, typically with pH or time-dependent coatings, such that the subject agent is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

Additional pharmaceutically acceptable carriers are known in the art and described in, e.g., Remington: The Science and Practice of Pharmacy, $22^{nd}$ revised edition (Allen Jr, L V, ed., Pharmaceutical Press, 2012). Liquid formulations can be solutions, emulsions or suspensions and can include excipients such as suspending agents, solubilizers, surfactants, preservatives, and chelating agents.

The preferred preparation is in a ready-to-use, storage stable form, with a shelf-life of at least one or two years.

The term "formulation" as used herein refers to a preparation ready-to-use in a specific way. Specifically, compositions described herein comprises the Azelastine compound, and a pharmaceutically acceptable diluent, carrier or excipient.

According to a specific aspect, formulations are provided comprising pharmaceutically acceptable vehicles for nasal, intrapulmonary, oral, topical, mucosal or parenteral administration. Administration may also be intradermal or transdermal. Also, the present disclosure includes such compounds, which have been lyophilized and which may be reconstituted to form pharmaceutically acceptable formulations for administration.

Specific medicinal products or pharmaceutical compositions described herein are formulated for intranasal administration or by another topical route e.g., onto biological surfaces, including e.g., mucosa or skin. Pharmaceutical carriers suitable for facilitating such means of administration are well known in the art.

Specifically, a nasal spray may be used containing 0.001% or 0.15% (w/w) Azelastine compound in an aqueous solution at pH 6.8±0.3, optionally further containing any one or more of citric acid monohydrate, disodium hydrogen phosphate dodecahydrate, edetate disodium, hypromellose, purified water, sodium chloride, and a preservative such as benzalkonium chloride.

To administer the Azelastine compound by any route other than parenteral administration, it may be necessary to coat the active agent with, or co-administer the active agent with, a material to prevent its inactivation. For example, an appropriate carrier may be used, for example, liposomes, or a diluent. Pharmaceutically acceptable diluents include saline and aqueous buffer solutions.

The Azelastine compound can be orally administered, for example, with an inert diluent or an assimilable or edible carrier. For example, a preparation may be enclosed in a hard- or soft-shell gelatin capsule, or compressed into tablets. For oral therapeutic administration, the Azelastine compound may be incorporated with excipients and used in the form of ingestible tablets, buccal tablets, troches, capsules, elixirs, suspensions, syrups, wafers, and the like. The percentage of the compound in the compositions and preparations may, of course, be varied. The amount of the Azelastine compound in such therapeutically useful compositions is such that a suitable dosage will be obtained.

Tablets will contain excipients, glidants, fillers, binders, disintegrants, lubricants, flavors and the like. Granules may be produced using isomaltose. It is furthermore preferred to provide for a preparation formulated to act at the site of the mucosa, e.g. at mucosal sites (such as nose, mouth, eyes, esophagus, throat, lung), e.g. locally without systemic action. Aqueous formulations are prepared in sterile form, and when intended for delivery by other than oral administration generally will be isotonic.

The term "mucosal" with respect to administration or application or else mucosal use of a preparation for treating a subject or a respective formulation, refers to administration via the mucosal route, including systemic or local administration, wherein an active ingredient is taken up by contact with mucosal surfaces. This includes nasal, pulmonary, oral, or peroral administration and formulations, e.g., liquid, syrup, lozenge, an eye drop, tablet, spray, powder, instant powder, granules, capsules, cream, gel, drops, suspension, or emulsion.

Peroral formulations may include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Other compositions useful for attaining systemic delivery of the Azelastine compound or respective preparations include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose, or glidants, lubricants, sweeteners, colorants, antioxidants and flavoring agents.

The Azelastine compound or respective preparations can also be administered topically to a subject, e.g., by the direct laying on or spreading of a composition containing same on the epidermal or epithelial tissue of the subject, or transdermally via a "patch". Such compositions include, for example, lotions, creams, solutions, gels and solids. These topical compositions may comprise an effective amount, usually at least about 0.001 wt %, or even from about 0.1 wt % to 5 wt %, or 1 wt % to about 5 wt %, of the Azelastine compound. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents and the like.

Pharmaceutical compositions suitable for injectable use include sterile aqueous solutions (in particular where the compounds or pharmaceutically acceptable salts are water soluble) or dispersions and sterile powders for the extemporaneous preparation of sterile injectable solutions or dispersion. In particular, the composition is specifically sterile and fluid to the extent that easy syringability exists; it is stable under the conditions of manufacture and storage and preserved against the contaminating action of microorganisms such as bacteria and fungi.

Suitable pharmaceutically acceptable vehicles include, without limitation, any non-immunogenic pharmaceutical adjuvants suitable for oral, parenteral, nasal, mucosal, transdermal, intravascular (IV), intraarterial (IA), intramuscular (IM), and subcutaneous (SC) administration routes, such as phosphate buffer saline (PBS).

The term "subject" as used herein shall refer to a warm-blooded mammalian, particularly a human being or a non-human animal, including e.g., dogs, cats, rabbits, horses, cattle, and pigs. In particular the treatment and medical use described herein applies to a subject in need of prophylaxis or therapy of a disease condition associated with a Coronaviridae virus infection and/or an infection with any of the other target viruses described herein. Specifically, the treatment may be by interfering with the pathogenesis of a disease condition where a Coronaviridae virus and/or an Adenoviridae virus and/or a Paramyxoviridae virus and/or a Orthomyxoviridae virus is a causal agent of the condition. The subject may be a patient at risk of such disease condition or suffering from disease. Specifically, the subject may have a weakened immune system or existing respiratory or cardiac disease which are more likely than others to increase the risk of disease or severity of disease.

The term "at risk of" a certain disease conditions, refers to a subject that potentially develops such a disease condition, e.g. by a certain predisposition, exposure to virus or virus-infected subjects, or that already suffers from such a disease condition at various stages, particularly associated with other causative disease conditions or else conditions or complications following as a consequence of viral infection. The risk determination is particularly important in a subject, where a disease has not yet been diagnosed. This risk determination therefore includes early diagnosis to enable prophylactic therapy. Specifically, the Azelastine compound is used in subjects with a high risk, e.g. a high probability of developing disease.

The term "patient" includes human and other mammalian subjects that receive either prophylactic or therapeutic treatment. The term "patient" as used herein always includes healthy subjects. The term "treatment" is thus meant to include both prophylactic and therapeutic treatment.

Specifically, the term "prophylaxis" refers to preventive measures which is intended to encompass prevention of the onset of pathogenesis or prophylactic measures to reduce the risk of pathogenesis.

The term "therapy" as used herein with respect to treating subjects refers to medical management of a subject with the intent to cure, ameliorate, stabilize, reduce the incidence or prevent a disease, pathological condition, or disorder, which individually or together are understood as "disease condition". The term includes active treatment, directed specifically toward the improvement of a disease condition, prophylaxis directed specifically toward the prevention of a disease condition, and also includes causal treatment directed toward removal of the cause of the associated disease condition. In addition, this term includes palliative treatment designed for the relief of symptoms rather than the curing of the disease condition, and further curing a disease condition directed to minimizing or partially or completely inhibiting the development of the associated disease condition, and supportive treatment employed to supplement another specific therapy directed toward the improvement of the associated disease condition.

The foregoing description will be more fully understood with reference to the following examples. Such examples are, however, merely representative of methods of practicing one or more embodiments of the present invention and should not be read as limiting the scope of invention.

EXAMPLES

Example 1

Antiviral Drug Identification

The development of mathematical representations for small molecules (drugs) is a research area of immense value for modern pharmaceutical research and thus numerous molecular descriptors have been developed and exploiting 2D and/or 3D features of chemical structures. These descriptors have been very valuable in assessing quantitative structure-activity relationships. Specifically, atom-centered feature pairs have turned out to be of great relevance for drug discovery programs as they provide cost-effective approaches to high-throughput structure-activity relationship analysis, compound selection, virtual chemical screening and pharmacological profiling. One of the commonly used chemical descriptors is referred to as SHED, for Shannon Entropy Descriptor (1). In this approach the topological distributions of atom-centered feature pairs are quantified based on information theory (Shannon entropy). The particular benefit is that chemically different but topologically related chemical scaffolds can be identified using the SHED approach.

In order to identify new anti-viral drugs, a drug identification strategy was used based on a biochemical pathway-based intervention strategy. Clinically approved drugs that match a predefined mechanistic profile (mode-of-action) were identified as candidate anti-viral drugs using a Shannon entropy-based description of the inherent chemical features of small molecules (drugs). The rationale behind this approach is that ligands with similar Shannon entropy vectors will bind to similar protein targets.

Here the DRUGBANK database (2) was used, a repository of approved drugs and their experimentally verified protein targets. Drug similarities were assessed by calculating Euclidean distances (0.25 was taken as a cutoff value).

As a starting point for the analysis, available mechanistic information on SARS-CoV-2 infection was extracted from recent bioinformatics analysis (3) together with analysis of certain query anti-viral compounds. The pathway profiles of the query anti-viral compounds with known SARS-CoV2 activity (hydroxychloroquine (RS)-2-[{4-[(7-Chlor-4-chinolinol)amino]pentyl}(ethyl)amino]ethanol, SSAA09E2 {N-[[4-(4-methylpiperazin-1-yl)phenyl]methyl]-1,2-oxazole-5-carboxamide}, and SSAA09E3 [N-(9,10-dioxo-9,10-dihydroanthracen-2-yl)benzamide]) were predicted using the Shannon entropy approach, and interestingly, showed significant mutual overlap.

Secondly, the pathway profiles for SARS inhibitors were predicted with well-defined mechanisms and mode of actions: SSAA09E2, a small molecule ACE2 inhibitor, and SSAA09E3, a general inhibitor of virus host membrane fusion (4). It was found that both inhibitors shared a considerable number of pathways with hydroxychloroquine. Summing up, the analysis showed that similar pathways are involved in SARS-CoV-2 infection, targeted by hydroxychloroquine and addressed by inhibitors with well-defined mechanisms. It was thus concluded that these pathways are highly relevant for antiviral activity and can serve as the basis for a novel drug repurposing for anti-viral activity by looking for clinically approved drugs that previously were not known to have anti-viral activity with matching pathway profiles.

Clinically approved drugs were explored for matching the individual pathway profiles. The predicted pathway profiles obtained for the different query compounds (hydroxychloroquine, SSAA09E2 and SSAA09E3) were employed to screen the SELLECKCHEM database of approved (and commercially available) drugs. The rationale for candidate selection was based on simultaneous appearance of approved drugs in the different (predicted) datasets. Hydroxychloroquine and SSAA09E2 (ACE2 inhibitor) showed significant overlap among each other and with drugs obtained with the SARS-CoV-2 pathway profile. After eliminating drugs based on chemical composition, two approved drugs were selected as candidate anti-virals for further testing in an in vitro SARS-CoV-2 infection model: Azelastine and Maraviroc.

REFERENCES (1) Gregori-Puigjane, E. and Mestres, J. SHED: Shannon Entropy Descriptors from Topological Feature Distributions. J. Chem. Inf. Model. 46, 1615-1622 (2006)

(2) Wishart, D S., Knox, C., Guo, A C: Cheng, D., Shrivastava, S., Tzur, D., Gautam, B. and Hassanali, M. DrugBank: a knowledgebase for drugs, drug action and drug targets. Nucleic Acids Res. D901-D906, (2008)

(3) Zhou, Y, Hou, Y., Shen, J, Huang, Y., Martin, W. and Cheng, F. Network-based drug repurposing for novel coronavirus 2019-nCoV/SARS-CoV-2. Cell Discovery 6,14-32, (2020)

(4) Adedeji, A O., Severson, W., Jonsson, C., Singh, K., Weiss S R. and Sarafanos, S G. Novel Inhibitors of Severe Acute Respiratory Syndrome Coronavirus Entry That Act by Three Distinct Mechanisms. J Virol. 87, 8017-8028, (2013)

Example 2

Preventing Virus Infection of Vero E6 Cells by SARS-CoV-2

To detect the effect of Azelastine-HCl on SARS-CoV-2 infection, the ACE2 expressing Vero E6 (monkey kidney) cells were infected with SARS-CoV-2 in the absence or presence of Azelastine-HCl and the cytopathogenic effect was evaluated by microscopic examination of the cells.

Experimental Procedure:

Vero E6 cells (ATCC CRL-1586) were seeded on 96-well plates. After 2 days the cell cultures reached confluency and formed a homogenous monolayer. The cells were fed with fresh cell culture medium (DMEM+ FBS?). Azelastine-HCl (Seleckchem cat #S2552, 10 mM stock solution dissolved in DMSO) and Maraviroc (Seleckchem cat #S2003, 10 mM stock solution dissolved in DMSO), an anti-HIV antiviral agent, were added to the cell culture medium at 50, 25, 12.5, 6.25 and 3.125 μM final concentrations (dilutions were prepared in culture medium). For viral infection the SARS-CoV-2 virus (hCoV-19/Hungary/SRC_isolate_2/2020, Accession ID: EPI_ISL_483637) was added to the supernatant at MOI 0.1 (multiplicity of infection: 1 viral particle to 10 cells) immediately after the culture medium exchange (basically simultaneously). The virus stock was prepared by propagation in Vero E6 cells and the infectious titre determined. After 30 min incubation with the virus, the culture medium was removed and replaced with fresh culture medium containing Azelastine-HCl or Maraviroc at the above concentrations (co-administration: simulating prevention). The experiments were also performed with Azelastine in a way when the drug was given only after the 30 min incubation with the virus, but not during this period (post-infection administration: post-exposure/therapeutic setting). 48 hours post infection the cells were evaluated by microscopic observation and then the supernatants were collected and stored at −80° C. for quantitative PCR analysis. Viral RNA was extracted from the culture supernatant samples with the Monarch Total RNA Miniprep Kit (New England BioLabs, Cat #: T2010S) according to the manufacturer's instructions. Briefly, 300 μl Lysis buffer was mixed with 100 μl culture supernatant, the gDNA contamination was removed with the dedicated column (retaining DNA), and the flow-through containing RNA was applied to the RNA-binding column. After washing the column, the RNA was eluted with $H_2O$, and samples stored at −80° C. till analysis. After the reverse transcription reaction, DNA was amplified with the F, R and P2 primers from the RdRp gene The primers and probes used were specific for the SARS-CoV-2 RdRp gene:

```
Reverse primer:
                                    (SEQ ID NO: 1)
CARATGTTAAASACACTATTAGCATA,

Forward primer:
                                    (SEQ ID NO: 2)
GTGARATGGTCATGTGTGGCGG,

Probe:
                                    (SEQ ID NO: 3)
FAM-CAGGTGGAACCTCATCAGGAGATGC-BBQ.
```

The droplet PCR kit was used (BioRad ddPCR™, Bio-Rad Laboratories GmbH, Germany). The results of the RT-PCR reaction were quantified and calculated as viral particle/μl.

Results:

The confluent, homogenous layer of cells (uninfected, FIG. 2A) is disrupted and "holes" appear indicating cell death due to the virus (FIG. 2B). In the presence of Azelastine-HCl at all tested concentrations, the SARS-CoV-2 infected cells were significantly protected from dying providing evidence of direct anti-viral effect (FIG. 2C-F). Maraviroc was not effective at all at lower concentrations, and even the higher concentrations (12.5 to 50 μM) had only marginal protective effect with high cytopathogenic scores (Table 1). Surprisingly, Azelastine turned out to be an effective antiviral substance, which is at least as effective as hydroxychloroquine.

These data suggest that an Azelastine compound was able to stop infection by SARS-CoV-2 immediately as soon as it was applied to the cells. Since the virus needs to enter cells to multiple and spread into the body, Azelastine is expected to prevent COVID-19 right at the place where the virus infects the human body, on the mucosal surfaces of the respiratory tract.

TABLE 1

| Compound | 50 μM | 25 μM | 12.5 μM | 6.25 μM | 3.125 μM |
|---|---|---|---|---|---|
| Azelastine-HCl | nd | 0 or 1 | 0 or 1 | 2 | 2 |
| Maraviroc | 3 | 3 | 3 | 4 | 4 |

nd: no data

Scoring:

0: no cytopathic effect (CPE), cells appeared to be the same as in the uninfected control 1: very small areas showed low level of CPE 2: CPE observed in small areas of the cell culture 3: stronger CPE, but not as strong as in the infected control 4: CPE is as strong as in the infected control Quantitative PCR analysis revealed that Azelastine was highly effective to reduce the viral particle numbers, both in a co-administration (simulating prevention) up to >99% and up to >97% in post-infection (simulating post-exposure or therapy) administration settings (Table 2) suggesting that Azelastine can be used in both prophylactic and therapeutic settings. As expected, the co-administration is more effective, but the low viral numbers at the 25 μm Azelastine concentration demonstrates that ongoing infection can be stopped not only prevented.

TABLE 2

| Azelastine | viral particle/μL | |
|---|---|---|
| concentration (μM) | co-administration | post-infection administration |
| 0 | 99.15 | 99.15 |
| 3.125 | 98.4 | 138 |
| 6.25 | 15.45 | 68.4 |
| 12.5 | 12.25 | 52 |
| 25 | 0.2 | 6.865 |

Numbers represent median values of up to 5 replicate samples/concentration with 2-3 technical repeats (quantitative PCR repeated from same biological sample).

Example 3

Efficacy Against Virus Infection of Reconstituted Human Nasal Tissue by SARS-CoV-2

To confirm the efficacy of Azelastine-HCl against SARS-CoV2 on human cells, reconstituted human nasal 3D tissue (MucilAir, 3D Human Airway Epithelia reconstituted in vitro) was infected with SARS-CoV-2 and treated with a commercial nasal spray containing Azelastine. The cytopathogenic effect was evaluated by microscopic examination of the tissue and virus particle number was determined by Droplet PCR.

Experimental Procedure:

MucilAir human nasal tissue generated from healthy donors (Epithelix San (Geneva, Switzerland), Cat #: EP02MP) was infected with SARS-CoV-2 (SARS-CoV-2 virus, hCoV-19/Hungary/SRC_isolate_2/2020, Accession ID: EPI_ISL_483637) at multiplicity of infection (MOI) of 0.01 on the apical side. After 20 min incubation at 37° C. in 5% $CO_2$, the virus containing media was removed completely. Then a 5-times diluted (in MucilAir culture medium) solution of the Allergodil nasal spray (0.1% azelastine-HCl, Mylan) was added onto the apical side (in 200 μl of volume) for 20 min. Following the treatment, the diluted nasal spray was fully removed from the surface of the cells to provide a liquid-air interface and incubated for 24 hours. The 20-min treatment with the diluted Allergodil was repeated at 24 and 48 hours post infection (hpi). After 24, 48 and 72 hpi the apical sides of the cells were washed for 15 min with MucilAir Culture medium and the solution collected for quantification of infective virus particles. The cells were also inspected under an inverted microscope at 48 and 72 hpi.

Total RNA was extracted from the apical washes (100 μl) using Monarch Total RNA Miniprep Kit (Promega, Cat #: T2010S) according to the manufacturer's instructions. As described in Example 2, for virus copy number quantification droplet digitalPCR technology was applied (Bio-Rad Laboratories Inc. QX200 Droplet Digital PCR System).

Results:

Microscopic analysis of tissues at 48 and 72 hours revealed reduced mucin production in infected cells, seen as complete lack of black spots in the microscopic image, relative to control cells (no virus or drug treatment, large amount of black material seen above the cells) (FIG. 3). Importantly, the mucin production, demonstrated by the presence of the black material in the microscopic image is clearly demonstrated in the presence of 5-fold diluted Allergodil treatment and comparable to that of seen in the negative control (no virus or drug treatment). No difference in tissue morphology was detected in control and azelastine-treated cells (without virus infection) and cilial movement was detected in all tissues.

Droplet Digital PCR analysis confirmed an effective SARS-CoV-2 infection and fast viral replication, reaching several thousand copies per microliter by 72 hours post-infection in the apical compartment of the tissue inserts. 5-fold diluted nasal spray (0.02% Azelastine HCl) used daily for 20 minutes drastically reduced the viral particle numbers by 48 and 72 hours post infection (>99.9% inhibition) (Table 3).

TABLE 3

| | virus particles/μl in apical wash (% relative to untreated) | | |
|---|---|---|---|
| | 24 h pi | 48 h pi | 72 h pi |
| untreated | 0.68 | 444.67 | 3521.33 |
| Allergodil 5× diluted | 0.05 (7.88%) | 0.03 (0.01%) | 0.05 (0.001%) |

Example 4

Demonstration of the In Vitro Potency of Azelastine Against SARS-CoV-2 Variants of Concern B.1.1.7 and the B.1.351

To detect the antiviral effect of azelastine-HCl on SARS-CoV-2 variant viruses, an ACE2 and TMPRSS2 expressing Vero (monkey kidney) cell line was infected with the B.1.1.7 and B.1.351 variants of concern in the absence or presence of azelastine-HCl and the effect on viral propagation was evaluated by quantitative PCR.

Experimental Procedure:

SARS-CoV-2 Infection Assay with Vero-TMPRSS2/ACE2

Vero cells stably overexpressing human serine protease TMPRSS2 and ACE2 receptor (Riepler et al, Comparison of Four SARS-CoV-2 Neutralization Assays. Vaccines (Basel), 2020; 9(1):13) were seeded on 96-well plates at $10^4$/well the day before infection. Azelastine hydrochloride, (Sigma-Aldrich, PHR1636-1G, Lot. #LRAC4832) dissolved in DMSO to a concentration of 10 mM, was diluted with Dulbeccos's Modified Eagle Medium (Merck, Darmstadt, Germany) containing 2% FBS to final concentrations ranging from 50 μM to 0.4 μM (2-fold serial dilutions). Prior to infection of the cells, cell culture supernatant was aspirated and replaced by 50 μl of the Azelastine-HCl dilutions in the preventive (co-administration) setting and 50 μl of medium in the post-infection setting. For each azelastine concentrations triplicate measurements were performed. Subsequently, cells were infected with SARS-CoV-2 isolates belonging either to the B.1.1.7 or the B.1.351 type at an MOI of 0.01 for 30 minutes at 37° C. For both experimental settings, the supernatant then was aspirated and replaced by 50 μl fresh medium and 50 μl of the same Azelastine concentrations used before, resulting in Azelastine concentrations ranging between 25 μM and 0.2 μM. 48 hours post infection, the cytopathic effect was evaluated and supernatant was mixed in a 1:1 ratio with DLR buffer (0.5% IGEPAL, 25 mM NaCl in 10 mM Tris-HCl buffer, 15 μl RiboLock RNase Inhibitor (ThermoScientific, 40 U/μl, EO0381 per ml DLR buffer) to isolate the viral RNA. SARS-CoV-2 genome copies were quantified via qPCR using E gene specific primers (5' ACA GGT ACG TTA ATA GTT AAT AGC GT 3" (SEQ ID NO:5) and 5' ATA TTG CAG CAG TAC GCA CAC A3" (SEQ ID NO:6)), FAM-labelled probe (FAM-ACA CTA GCC ATC CTT ACT GCG CTT CG-BHQ1 (SEQ ID NO:7)) and iTaq Universal Probes One-Step Kit (BioRad, Cat. #1725141). An in-house produced in vitro transcribed RNA standard (E gene of SARS-CoV-2) was used to quantify qPCR results. Virus only wells without azelastine treatment were set to 100% and percent inhibition was calculated for each sample relative to the virus only wells.

Results:

Quantitative PCR analysis revealed that Azelastine was highly effective to reduce the viral particle numbers, both in a preventive (co-administration)) and post-infection (simulating post-exposure or therapy) administration settings (Tables 4 & 5 and FIGS. 4A and 4B). Similar to the results with the wild-type virus, the co-administration is somewhat more effective, but the low viral numbers (over 90% inhibition) at the 12.5 μm azelastine concentration demonstrate that ongoing infection can be stopped not only prevented. The effective azelastine concentration needed to inhibit 50% of the infection (EC50) was between 4 and 6.5 μM depending on the setting and the virus mutant, which is in the range of the EC50 observed for the wild-type virus (~6 μM). This demonstrates that the efficacy of azelastine against SARS-COV-2 is independent of the emerging high risk mutations.

TABLE 4

| B.1.351 | | |
|---|---|---|
| Azelastine | inhibition of infection (relative to no azelastine treated cells) | |
| concentration (μM) | preventive setting | therapeutic setting |
| 3.125 | 32.87% | 22.01% |
| 6.25 | 74.86% | 54.97% |
| 12.5 | 99.12% | 97.62% |

Numbers represent mean values of 3 independent experiments each with 3 replicate samples (9 in total)/concentration

TABLE 5

| B1.1.7 | | |
|---|---|---|
| Azelastine | inhibition of infection (relative to no azelastine treated cells) | |
| concentration (μM) | preventive setting | therapeutic setting |
| 3.125 | 23.76% | 2.57% |
| 6.25 | 72.79% | 47.40% |
| 12.5 | 98.81% | 91.71% |

Numbers represent mean values of 2 independent experiments each with 3 replicate samples (6 in total)/concentration Conclusion:

These data suggest that an azelastine compound was able to stop infection by SARS-CoV-2 mutants B.1.351 and B.1.1.7 immediately as soon as it was applied to the cells. Since the virus needs to enter cells to multiply and spread into the body, azelastine is expected to prevent COVID-19 right at the place where the virus infects the human body, on the mucosal surfaces of the respiratory tract.

Example 5

Preventing Virus Infection of Calu-3 Cells by SARS-CoV-2

To confirm the anti-viral effect of Azelastine-HCl on cells expressing the surface protease TMPRSS2, the human lung adenocarcinoma cell line, Calu-3 was infected with SARS-CoV-2 in the absence or presence of Azelastine-HCl and the viral particle number was measured after 48 h.

Experimental Procedure:

Calu-3 (ATCC® HTB-55™) were seeded on 96-well plates. 2 days later, when the cells reached confluency, cultures were fed with fresh cell culture medium (EMEM+10% FBS+1% P/S, 1% L-Glutamine, 1% Non-essential amino acid). Azelastine-HCl (Seleckchem cat #S2552, 10 mM stock solution dissolved in DMSO) and Hydroxychloroquine Sulfate (TCI cat. #H1306, 10 mM stock dissolved in H2O and sterile filtered) were added to the cell culture medium at 50 and 25 μM final concentrations (dilutions were prepared in culture medium). Hydroxychloroquine sulfate has strong anti-SARS-CoV-2 effect on Vero E6 cells (not expressing TMPRSS2), but significantly loses its potency when tested on cells expressing the surface protease TMPRSS2, including Calu-3 cells (ref. Hoffmann et al. Nature 2020, 585:588-590).

The virus stock was prepared by propagation in Vero E6 cells and the infectious titre determined. For viral infection the SARS-CoV-2 virus was added to the supernatant at MOI 0.01 (multiplicity of infection: 1 viral particle to 100 cells) immediately after the culture medium exchange (basically simultaneously). After 30 min incubation with the virus, the culture medium was removed and replaced with fresh culture medium containing Azelastine-HCl or Hydroxychloroquine sulfate at the above concentrations. 48 hours post infection the supernatants were collected and stored at −80° C. for quantitative PCR analysis. Viral RNA was extracted from the culture supernatant samples with the Monarch Total RNA Miniprep Kit (New England BioLabs, Cat #: T2010S) according to the manufacturer's instructions. Briefly, 300 μl Lysis buffer was mixed with 100 μl culture supernatant, the gDNA contamination was removed with the dedicated column (retaining DNA), and the flow-through containing RNA was applied to the RNA-binding column. After washing the column, the RNA was eluted with $H_2O$, and samples stored at −80° C. till analysis. After the reverse transcription reaction, DNA was amplified with the F, R and P2 primers from the RdRp gene using the 1-Step RT-ddPCR Advanced Kit for Probes (BioRad ddPCR™, cat #1864021 and 1864022, https://www.bio-rad.com/de-at/product/1-step-rt-ddpcr-advanced-kit-for-probes?ID=NTGCRI15).

Primers and probes, real-time RT-PCR for 2019 novel coronavirus

| Assay/use | Oligonucleotide | Sequence[a] |
|---|---|---|
| RdRP gene | RdRp_SARSr-F | GTGARATGGTCATGTGTGGCGG SEQ ID NO: 8 |
| | RdRp_SARSr-P2 | FAM-CAGGTGGAACCTCATCAGGAGATGC-BBQ SEQ ID NO: 9 |
| | RdRP_SARSr-P1 | FAM-CCAGGTGGWACRTCATCMGGTGATGC-BBQ SEQ ID NO: 10 |
| | RdRp_SARSr-R | CARATGTTAAASACACTATTAGCATA SEQ ID NO: 11 |
| E gene | E_Sarbeco_F | ACAGGTACGTTAATAGTTAATAGCGT SEQ ID NO: 12 |
| | E_Sarbeco_P1 | FAM-ACACTAGCCATCCTTACTGCGCTTCG-BBQ SEQ ID NO: 13 |
| | E_Sarbeco_R | ATATTGCAGCAGTACGCACACA SEQ ID NO: 14 |
| N gene | N_Sarbeco_F | CACATTGGCACCCGCAATC SEQ ID NO: 15 |
| | N_Sarbeco_P | FAM-ACTTCCTCAAGGAACAACATTGCCA-BBQ SEQ ID NO: 16 |
| | N_Sarbeco_R | GAGGAACGAGAAGAGGCTTG SEQ ID NO: 17 |

[a]W is A/T; R is G/A; M is A/C; S is G/C. FAM: 6-carboxyfluorescein; BBQ: blackberry quencher.
[b] Optimised concentrations are given in nanomol per liter (nM) based on the final reaction mix, e.g. 1.5 μL of a 10 μM primer stock solution per 25 μL total reaction volume yields a final concentration of 600 nM as indicated in the table above.

The results of the RT-PCR reaction were quantified and calculated as viral copy number/μl and compared to the copy number measured in infected mock-treated (buffer) cells (positive control).

Simultaneously, cell survival was measured on non-infected Calu-3 cells treated with azelastine-HCl or hydroxychloroquine sulfate for 48 h, with the CellTiter-Glo® 2.0 Cell Viability Assay (Promega® cat. #G9241) according to the manufacturer's instructions. Briefly, CellTiter-Glo® 2.0 Reagent was added at volume equal to that of the medium to the cells and incubated for 10 minutes at room temperature. Luminescence signal was measured and compared to the signal measured with cells untreated (negative control).

Results:

Quantitative PCR analysis revealed that Azelastine-HCl was highly effective in reducing the viral particle numbers on human lung adenocarcinoma cells up to >99% at 50 μM concentration and over 90% at 25 μM concentration (FIG. 6) confirming that Azelastine exserts its anti-SARS-CoV-2 effect on human respiratory epithelial cells expressing the surface protease TMPRSS2 and the most relevant for SARS-CoV-2 infection.

Example 6

Preventing and Treating Infection of HEp-2 Cells by Respiratory Syncytial Virus (RSV)

To confirm the broad anti-viral effect of azelastine-HCl HEp-2 cells (ATCC CCL-23) were infected with RSV in the absence or presence of azelastine-HCl. Azelastine-HCl was tested in 3 settings: preventive (azelastine-HCl treatment followed by infection), co-administration (cells infected and treated with azelastine-HCl simultaneously) and in therapeutic settings (infected cells treated with azelastine-HCl 1 h post-infection). Spot number and viral genome copy number was determined and compared to cells treated with buffer.

Experimental Procedure:

Azelastine-HCl (Sigma cat #PHR1636-1G) was tested for anti-RSV activity in the 0.4 to 25 μM concentration range, using a 10 mM stock prepared in DMSO.

$1\times10^4$ HEp-2 cells (ATCC CCL-23) were seeded in 96-well plates and cultured in 50 μl/well of DMEM media supplemented with 10% FCS and 2 mM L-glutamine at 37° C. at 5% $CO_2$ and 100% humidity for 3 hours. After 3 hours, cells reached adherence and were infected with RSV Long strain (ATCC VR-26, kindly provided by T. Grunwald, Fraunhofer Institute for Cell Therapy and Immunology, Leipzig, Germany) at MOI 0.01. Azelastine-HCl was added to the cells either 1 h prior to infection, simultaneously with the infection or 1 h post-infection. The azelastine-HCl stock was serially diluted with culture media (DMEM/10% FCS/2 mM L-glutamine) to reach the intended final concentration. DMSO was diluted the same way and added to cells as vehicle control. Cells infected and treated in a total volume of 200 μl were incubated for 48 h at 37° C. at 5% $CO_2$ and 100% humidity. RSV infected plaques were determined by immunocytochemical staining with polyclonal goat antibody against RSV (anti-RSV Gt X (IgG Frac), Merck) and HRP-conjugated rabbit polyclonal anti-goat IgG (Novusbio). 3-Amino-9-ethylcarbazole (AEC, Sigma) was used as a chromogen in immunohistochemistry to visualize RSV infected cells. Spots were counted manually. Viral genome copy number was determined by RT-PCR using primers RSV-1 (5'-AGA TCA ACT TCT GTC ATC CAG CAA-3', SEQ ID NO:18) and RSV-2 (5'-GCA CAT CAT AAT TAG GAG TAT CAA T-3', SEQ ID NO:19) as described previously by Wilmschen et al. (Vaccines, 2019, 7:59). The Ct value obtained after azelastine-HCl treatment was compared to vehicle treated cells only. For calculating the viral genome copy number in the treated samples relative to vehicle, we used the following equation: 1 Ct increase equals 50% lower copy number.

Cytotoxicity of azelastine-HCl towards HEp-2 cells was determined with a flow cytometry-based assay using the vital dye propidium iodide.

Experiments were performed 3-4 times independently.

Results:

Azelastine-HCl showed cytotoxicity to the HEp-2 cells at 12.8 and 25.6 μM concentration (FIG. 7). Therefore, the effect of azelastine-HCl was evaluate at 6.4 μM and lower concentrations. The RSV infection of cells, determined by spot count was reduced to ~50% at 3.2 and 6.4 μM concentrations compared to the vehicle (DMSO) treated controls (FIGS. 8A, 8B, and 8C) in all 3 settings suggesting a potent preventive and therapeutic effect of azelastine-HCl on RSV infection of HEp-2 cells. Viral genome copy number determination confirmed this effect at 6.4 μM azelastine-HCl concentration (Table 6).

TABLE 6

Effect of treatment with 6.4 μM azelastine-HCl on viral genome copy number in HEp-2 cells infected with RSV

| | Co-administration | preventive | therapeutic | DMSO (buffer control) |
|---|---|---|---|---|
| Ct (experiment #1) | 27.99 | 27.5 | 27.95 | 26.89 |
| Ct (experiment #2) | 27.21 | 27.17 | 27.27 | 26.3 |
| Viral genome copy relative to DMSO (experiment #1) | 46.65% | 65.52% | 47.96% | 100% |
| Viral genome copy relative to DMSO (experiment #2) | 53.22% | 54.71% | 51.05% | 100% |

Ct: cycle threshold in PCR reaction

Example 7

Preventing Infection of MucilAir™ by Influenza a Virus H1N1

The effect of repeated dose azelastine-HCl nose spray (Pollival, UrsaPharm Arzneimittel) upon influenza H1N1 infection was tested on fully differentiated human nasal epithelial cells cultured at the air-liquid interface (MucilAir™ Pool, Epithelix Sarl—primary cells from a pool of 14 different normal nasal donors).

Experimental Procedure:

Antiviral effect of azelastine-HCl against influenza H1N1 was tested as described by Boda et al (Antiviral Research 156 (2018) 72-79). Briefly, following apical wash of MucilAir™ Pool with MucilAir™ culture media (200 μl for 10 min), 10 μl of Azelastine-HCl at 0.02 or 0.01% concentration diluted from the nose spray Pollival® (Ursapharm Arzneimittel GmbH) with its own diluent was applied to the apical side of MucilAir™ for 10 minutes. Afterwards, 100 μl of influenza H1N1 (ATCC VR-95), from a stock of $10^6$ genome copy number per ml) was applied on the apical side and incubated for 3 h. The inoculum was washed away by washing the apical side of the cells with 200 μl of MucilAir culture media (20 min incubation) thrice. After the $3^{rd}$ wash, the same concentration of azelastine-HCl was added to the apical side of the cells at 10 μl volume and incubated for 21 h. At 24 h, 48 and 72 h timepoints MucilAir™ cell washes were repeated after which azelastine being replaced on the apical side as before. Viral copy numbers were determined from the apical washes at each timepoint. The basal culture medium was also removed and replaced with 500 μl of fresh culture medium, daily. From the basal wash LDH release was measured (to assess cell death at 96 h) as well as cytokine levels (IL-8 and RANTES) were determined at the 48 h and 96 h timepoints. All incubation steps were carried out at 34° C. at 5% $CO_2$ and at 100% humidity. Viral copy number was determined from the apical washed: for this RNA was extracted with the QIAamp® Viral RNA kit (Qiagen) and the viral RNA was quantified by RT-PCR (QuantyTect Probe RT-PCR, Qiagen) with the qTOWER3 detection system. Ct data were reported to the standard curve and expressed as genome copy number/ml.

As negative control, uninfected cells were included. As positive control, cells infected with influenza H1N1 but treated with buffer only were used. Antiviral effect of azelastine-HCl was compared to the effect of oseltamivir carboxylate (oseltamivir from Carbosynth, Compton, UK, at 10 μM) added to infected cells in the basolateral compartment. Compounds were tested in triplicates.

Results:

Treatment of MucilAir™ cells with azelastine-HCl at both concentrations resulted in a statistically significantly decrease in viral genome copy at 24 h post-infection, compared to buffer treated cells. The decrease in the viral copy was ~1.9 log (98.74% reduction) at 0.02% azelastine-HCl and ~0.9 log (87.4% reduction) at 0.01% azelastine-HCl (FIG. 9).

Additionally, azelastine-HCl showed anti-inflammatory effect during H1N1 infection of MucilAir™, both IL-8 (FIG. 10/A) and RANTES (FIG. 10/B) levels were significantly reduced compared to buffer control at day 2 and day 4 post-infection.

Azelastine-HCl at 0.02% concentration showed slight cytotoxicity (6.5%) in non-infected cells, but no cytotoxicity in infected cells or at the lower (0.01%) concentration.

Example 8

Preventing and Treating Infection of A549 Cells by Adenovirus

To confirm the broad anti-viral effect of Azelastine-HCl human lung carcinoma cells (A549) were infected with adenovirus in the absence or presence of Azelastine-HCl. Azelastine-HCl was tested in both a co-administration and a therapeutic setting.

Experimental Procedure:

Azelastine-HCl (Sigma cat #PHR1636-1G) was tested for anti-adenovirus activity in the 0.78 to 50 μM concentration range, using a 10 mM stock prepared in DMSO.

$3\times10^4$ A549 cells (ATCC CCL-185™) were seeded into 96-well plates in 100 μl complete growth medium (DMEM, high glucose, GlutaMAX™ supplement, with 10% FBS, QUALIFIED, HI 500 ML, Catalog #: 10500064, Lot #: 08Q6291K) and incubated at 37° C. at 5% $CO_2$ and 100% humidity. 24 h later, 25 μl fresh medium was added to the cells with MOI 0.01 TCID50 of adenovirus hAdv5 (ATCC VR-5) to initiate the infection. In the co-administration setting 25 μl of azelastine-HCl diluted in complete growth medium was added to the cells simultaneous with the infection. In the therapeutic setting, azelastine-HCl was added to the cells 6 h post-infection. Cells were incubated 48 hours post-infection at 37° C. at 5% $CO_2$ and 100% humidity. Afterwards plate was frozen at −80° C. and virus was released from cells by 3-time freeze-thaw cycles. Virus titer was determined by Adeno-X™ Rapid Titer kit (3 repeats per well, Clontech, Takara Bio, cat. #PT3651-2) following the manufacturer's instructions.

Cytotoxicity of azelastine towards uninfected A549 cells was determined with the CellTiter Glo Assay (Promega, USA) using the same protocol as described above, only without infecting the cells with adenovirus.

The invention claimed is:

1. A method of providing prophylactic or therapeutic antiviral treatment to a subject infected or at risk of being infected with one or more viruses, comprising the step of administering an antiviral effective amount of a pharmaceutical preparation comprising an Azelastine compound to the subject, wherein the Azelastine compound is administered as the sole antiviral substance, and wherein said one or more viruses are a coronaviridae virus, a respiratory syncytial virus (RSV), or an influenza A virus.

2. The method of claim 1, wherein:

the coronaviridae virus is any one of SARS-COV-2, MERS-COV, SARS-COV-1, HCoV-OC43, HCoV-HKU1, HCoV-NL63, HCoV-229E or PEDV; or the influenza A virus is H1N1, H3N3, or H5N1.

3. The method of claim 2, wherein said coronaviridae virus is a naturally-occurring SARS-COV-2 variant or mutant.

4. The method of claim 3, wherein said SARS-COV-2 variant or mutant comprises one or more mutations of the SARS-COV-2 S-protein.

5. The method of claim 4, wherein said one or more mutations of the SARS-COV-2 S-protein comprise any one or more of K417N, L452R, N501Y, D614G, P681H, P681R, E484K, E484Q, or a 69/70 deletion in SEQ ID NO:4.

6. The method of claim 3, wherein said SARS-COV-2 variant or mutant is selected from the group consisting of B.1.1.7, B.1.351, P.1, B.1.617, and B.1.618 mutants.

7. The method of claim 1, wherein the pharmaceutical preparation comprises a pharmaceutically acceptable carrier.

8. The method of claim 1, wherein the antiviral effective amount is effective in preventing infection of susceptible cells by the virus, thereby treating the disease condition.

9. The method of claim 1, wherein the antiviral effective amount is 0.1-500 μg/dose.

10. The method of claim 1, wherein said pharmaceutical preparation is formulated for local administration.

11. The method of claim 10, wherein said local administration is applied to the upper and lower respiratory tract, or is applied by nasal, pulmonary, intraoral, ocular, or dermal administration.

12. The method of claim 1, wherein said pharmaceutical preparation is administered to the subject as a spray, a powder, a gel, an ointment, a cream, a foam, a liquid solution, a lotion, a gargle solution, an aerosolized powder, an aerosolized liquid formulation, granules, capsules, drops, tablet, syrup, lozenge, eye drops, or a preparation for infusion or injection.

13. The method of claim 1, wherein the Azelastine compound is applied into the subject's nose in an amount of 1-1000 μg per nostril.

14. The method of claim 1, wherein the subject is a human being.

15. The method of claim 1, wherein the pharmaceutical preparation is administered to the subject's mucosa.

16. The method of claim 15, wherein the pharmaceutical preparation is formulated for local administration.

17. The method of claim 16, wherein local administration comprises application to the upper and lower respiratory tract or administration by nasal, pulmonary, intraoral, or ocular application.

18. The method of claim 15, wherein the pharmaceutical preparation is formulated for mucosal administration.

19. The method of claim 15, wherein the pharmaceutical preparation is administered to the subject by a nasal spray.

20. The method of claim 19, wherein the nasal spray contains between 0.001% and 0.15% (w/w) Azelastine compound in an aqueous solution at pH 6.8±0.3.

21. The method of claim 19, wherein the pharmaceutical preparation is administered to the subject by a plurality of doses of up to 10 per day.

22. The method of claim 1, wherein the antiviral effective amount is effective in preventing infection of susceptible cells by said one or more viruses.

23. The method of claim 1, wherein the subject has been infected or is at risk of being infected with said virus.

24. The method of claim 1, wherein the Azelastine compound is administered in combination with one or more active substances selected from the group consisting of anti-inflammatory and antibiotic substances.

25. The method of claim 1, wherein the subject is a human being, dog, cat, horse, camelid, cattle or pig.

* * * * *